US007083787B2

(12) United States Patent
Duke et al.

(10) Patent No.: US 7,083,787 B2
(45) Date of Patent: Aug. 1, 2006

(54) YEAST-DENDRITIC CELL VACCINES AND USES THEREOF

(75) Inventors: Richard C. Duke, Denver, CO (US); Donald Bellgrau, Silverthorne, CO (US); Alex Franzusoff, Denver, CO (US); Cara C. Wilson, Golden, CO (US)

(73) Assignees: GlobeImmune, Inc., Louisville, CO (US); The Regents of the University of Colorado, Boulder, CO (US)

( * ) Notice: Subject to any disclaimer, the term of this patent is extended or adjusted under 35 U.S.C. 154(b) by 303 days.

(21) Appl. No.: 09/991,363

(22) Filed: Nov. 15, 2001

(65) Prior Publication Data

US 2006/0104986 A1   May 18, 2006

Related U.S. Application Data

(60) Provisional application No. 60/249,173, filed on Nov. 15, 2000.

(51) Int. Cl.
   *A61K 39/00*   (2006.01)
   *A61K 45/00*   (2006.01)
   *C12N 1/00*    (2006.01)
   *C12N 1/16*    (2006.01)

(52) U.S. Cl. .............................. 424/184.1; 424/93.51; 424/278.1; 435/255.1

(58) Field of Classification Search ............. 424/155.1, 424/184.1, 185.1, 192.1, 193.1, 196.11, 274.1, 424/277.1, 278.1, 93.1, 93.2, 93.21, 93.5, 424/93.51, 93.7, 517; 435/6, 7.1, 7.2, 7.21, 435/7.31, 41, 69.1, 69.3, 325, 355, 372, 375, 435/254.1, 254.2, 254.21, 254.23, 320.1, 435/101, 243, 254, 255.1, 255.2; 436/69; 511/2, 49; 536/23.1, 23.5, 123.12
See application file for complete search history.

(56) References Cited

U.S. PATENT DOCUMENTS

| | | | |
|---|---|---|---|
| 4,775,622 A | 10/1988 | Hitzeman et al. | 435/68 |
| 5,413,914 A | 5/1995 | Franzusoff | 435/23 |
| 5,830,463 A | 11/1998 | Duke et al. | 424/93.51 |
| 5,858,378 A | 1/1999 | Bostwick | 424/274.1 |
| 5,919,651 A | 7/1999 | Hitzeman et al. | 435/69.1 |
| 6,187,307 B1* | 2/2001 | Cohen | 424/93.21 |
| 6,558,951 B1* | 5/2003 | Tomai et al. | 435/377 |
| 2002/0155108 A1* | 10/2002 | Barbera-Guillem | 424/140.1 |
| 2003/0035810 A1* | 2/2003 | Caplan | 424/199.1 |

FOREIGN PATENT DOCUMENTS

FR   2486400   *  9/1980

OTHER PUBLICATIONS

Definition "therapeutic", Stedman's OnLine Medical Dictionary, 27th Ed., www,sledmans.com.*
Translation of Massot et al. reference (French Patent 2,486,400).*
Brossier et al., Functional Analysis of the Carboxy-Terminal Domain of *Bacillus anthracis* Protective Antigen, Infection and Immunity, vol. 67 No. 2, pp. 964-967 (Feb. 1999).*
Sousa et al., Journal of Experimental Medicine, vol. 178 No. 2, pp. 509-519 (Aug. 1993).*
Kaur et al., Topics in HIV Medicine, vol. 11 No. 3, pp. 76-85 (2003), (no date available).*
Garber et al., AIDS Reviews, vol. 5 No. 3, pp. 131-139 (2003), (no date available).*
Layton et al. Immunology, vol. 87 No. 2, pp. 171-178 (1996), (no date available).*
Adams et al. International Reviews of Immunology, vol. 11 No. 2, pp. 133-141 (1994), (no date available).*
Paglia et al., Journal of Experimental Medicine, vol. 183 No. 1, pp. 317-322 (1996), (no date available).*
Allsopp et al., European Journal of Immunology, vol. 26 No. 8, pp. 1951-1959 (1996), (no date available).*
Bachmann et al., 1994, *Curr. Op. Immunol.*, 6:320-326, (no date available).
Baker et al., 1988, *Cell*, 54:335-344, (no date available).
Bizzini et al., 1990, *FEMS Microbiol. Immunol.*, 64:155-168, (no date available).
Bourdette et al., 1994, *J. Immunol.*, 152:2510-2519, (no date available).
Brake et al., 1984, *Proc. Natl. Acad. Sci. USA*, 81:4642-4646, (no date available).
Brown, D., 1995, *The Washington Post*, "Gene Therapy 'Oversold' by Researchers, Journalists", (no date available).
Chou et al., 1994, *J. Immunol.*, 152:2520-2529, (no date available).
Coghlan, 1995, *New Scientists*, 145:14-15, (no date available).
Cohen, 1994, *Science*, 264:1660, (no date available).
Cohen, 1994, *Science*, 264:1839, (no date available).
Davies et al., 1992, *Nucleic Acids Res.*, 20(11):2693-2698, (no date available).
Demmer et al., 1993, *J. Immunol.*, 150(12):5371-5378, (no date available).
Engelhardt et al., 1994, *Hum. Gene Ther*, 5:1217-1229, (no date available).
Fattal-German et al., 1992, *Develop. Biol. Standard.*, 77:115-120, (no date available).

(Continued)

*Primary Examiner*—James C. Housel
*Assistant Examiner*—Zachariah Lucas
(74) *Attorney, Agent, or Firm*—Sheridan Ross P.C.

(57) ABSTRACT

Disclosed is a vaccine that includes a dendritic cell loaded with a yeast vehicle and antigen. Also disclosed are methods of making the vaccine and using the vaccine to elicit cellular and humoral immune responses in a mammal. Additionally, a method to elicit an immune response by administration of a yeast vehicle and an antigen that is not complexed to the yeast vehicle is disclosed.

17 Claims, 21 Drawing Sheets

OTHER PUBLICATIONS

Franzusoff et al., 1995, *J. Biol. Chem.*, 270(7):3154-3159, (no date available).

Fujita et al., 1987, *Bulletin of the World Health Organization*, 65(3):303-308, (no date available).

Gnirke et al., 1991, *EMBO J.*, 10(7):1629-1634, (no date available).

Gobin et al., 1995, *Gene*, 163:27-33, (no date available).

Hatsuyama et al., 1994, *Plant Cell Physiol.*, 35(1):93-98, (no date available).

Ketner et al., 1994, *Proc. Natl. Acad. Sci. USA*, 91:6186-6190, (no date available).

Markie et al., 1993, *Somat. Cell Mol. Genet.*, 19(2):161-169, (no date available).

Marshall, 1995, *Science* 269:1050-1055, (no date available).

Moore et al., 1996, *FASEB J.*, 10(6) Abstract 2725, (no date available).

Moulard et al., 1994, *Eur. J. Biochem.* 225:565-572, (no date available).

Mullen et al., 1994, *Plant Physiol.*, 105:113 (Abstr. 606), (no date available).

Mulligan, 1993, *Science*, 260:926-931, (no date available).

Pachnis et al., 1990, *Proc. Natl. Acad. Sci. USA*, 87:5109-5113, (no date available).

Peterson et al., 1993, *Proc. Natl. Acad. Sci. USA*, 90:11207-11211, (no date available).

Rabinovich et al., 1994, *Science*, 265:1401-1404, (no date available).

Sanchez-Pascador et al., 1985, *Science*, 227:484-492, (no date available).

Schreuder et al., 1996 *Vaccine*, 14(5):383-388, (no date available).

Stern et al., 1992, *Cell*, 68:465-477, (no date available).

Suda et al., 1993, *Cell*, 75:1169-1178, (no date available).

Valenzuela et al., 1985 *Bio/Technology* 3:323-326, (no date available).

* cited by examiner

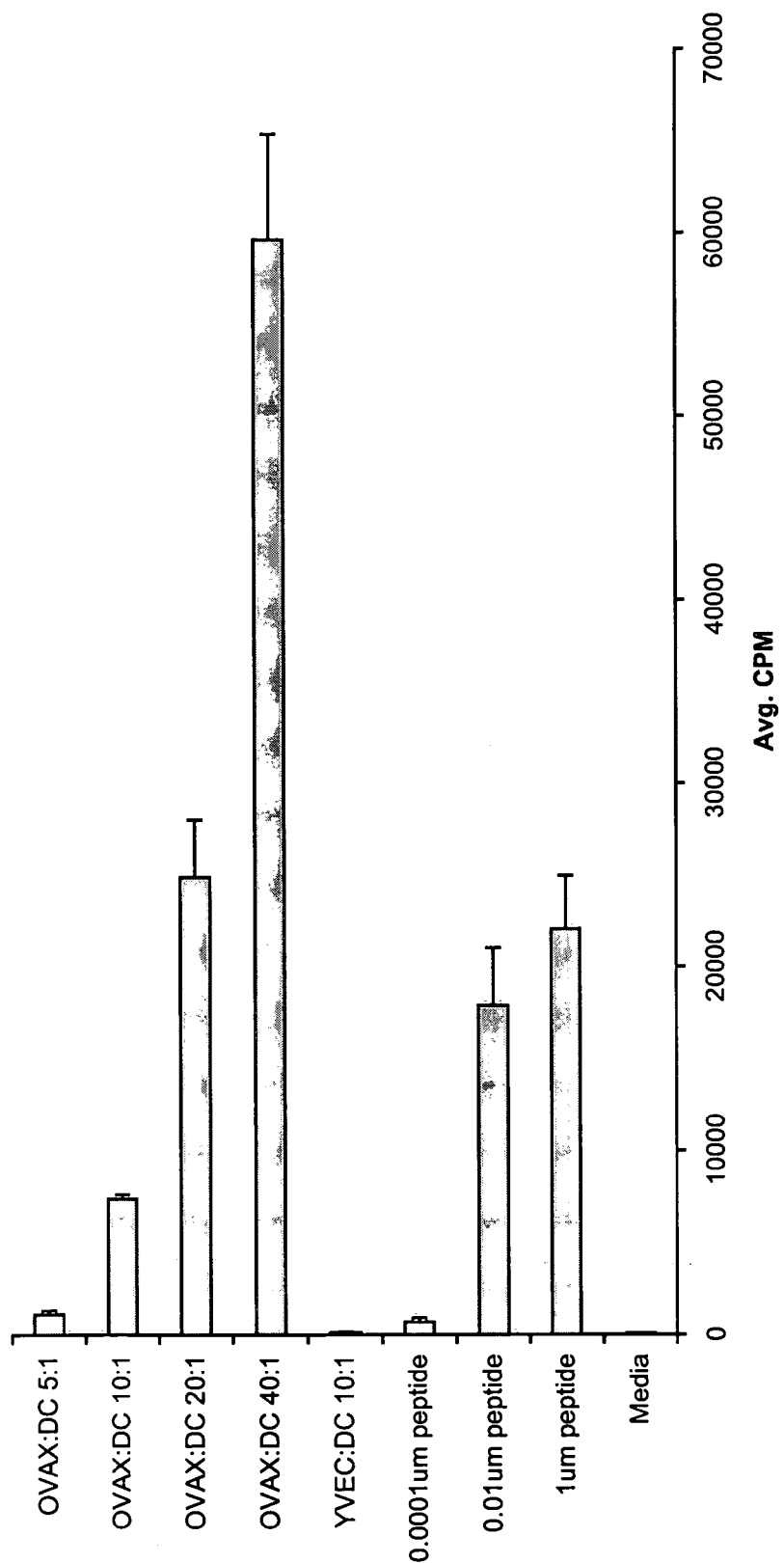

YEAST-DENDRITIC CELL VACCINES AND USES THEREOF

CROSS-REFERENCE TO RELATED APPLICATIONS

This application claims the benefit of priority under 35 U.S.C. § 119(e) from U.S. Provisional Application Ser. No. 60/249,173, filed Nov. 15, 2000, and entitled "Whole Recombinant Yeast Vaccine Activates Dendritic Cells and Elicits Protective Cell-Mediated Immunity". The entire disclosure of U.S. Provisional Application Ser. No. 60/249,173 is incorporated herein by reference.

GOVERNMENT RIGHTS

This invention was made in part using funding provided by Grant Nos. AI-01459, AI-33299, AI-34747, AI-42688, AI-42704, AI-43143 and CA-46934, all awarded by the National Institutes of Health. The government may have certain rights to this invention.

FIELD OF THE INVENTION

The present invention is directed to yeast-based vaccines and their use as a component of a dendritic cell vaccine.

BACKGROUND OF THE INVENTION

Vaccines are widely used to prevent disease and to treat established diseases (therapeutic vaccines). There remains, however, an urgent need to develop safe and effective vaccines and adjuvants for a variety of diseases, including those due to infection by pathogenic agents, cancers and other disorders amenable to treatment by elicitation of an immune response.

Protein antigens (e.g. subunit vaccines, the development of which was made possible by recombinant DNA technology), when administered without adjuvants, induce weak humoral (antibody) immunity and have therefore been disappointing to date as they exhibit only limited immunogenicity. An additional disadvantage of subunit vaccines, as well as of killed virus and recombinant live virus vaccines, is that while they appear to stimulate a strong humoral immune response when administered with adjuvants, they fail to elicit protective cellular immunity. Adjuvants are used experimentally to stimulate potent immune responses in mice, and are desirable for use in human vaccines, but few are approved for human use. Indeed, the only adjuvants approved for use in the United States are the aluminum salts, aluminum hydroxide and aluminum phosphate, neither of which stimulates cell-mediated immunity. Aluminum salt formulations cannot be frozen or lyophilized, and such adjuvants are not effective with all antigens. Moreover, most adjuvants do not lead to induction of cytotoxic T lymphocytes (CTL). CTL are needed to kill cells that are synthesizing aberrant proteins including viral proteins and mutated "self" proteins. Vaccines that stimulate CTL are being intensely studied for use against many viruses (e.g., HIV, HCV, HPV, HSV, CMV, EBV), intracellular bacteria (e.g., tuberculosis); intracellular parasites (e.g., malaria, leishmaniasis, shistosomiasis, leprosy), and all cancers (e.g., melanoma, prostate, ovarian, etc.). Thus adjuvants are needed that stimulate CTL and cell-mediated immunity in general.

Yeast have been used in the production of subunit protein vaccines, including those tested in the aforementioned HIV vaccine trials and the currently licensed hepatitis B vaccine; however, in this case yeast are used to produce the protein, but the yeast cells or subcellular fractions thereof are not actually delivered to the patient. Yeast have also been fed to animals prior to immunization to try to prime the immune response in a non-specific manner (i.e., to stimulate phagocytosis as well as the production of complement and interferon). The results have been ambiguous, and such protocols have not generated protective cellular immunity; see, for example, Fattal-German et al., 1992, *Dev. Biol. Stand.* 77, 115–120; Bizzini et al., 1990, *FEMS Microbiol. Immunol.* 2, 155–167.

U.S. Pat. No. 5,830,463, issued Nov. 3, 1998, to Duke et al. described the use of nonpathogenic yeast carrying at least one compound capable of modulating an immune response, and demonstrated that such complexes are efficacious at stimulating cell-mediated, as well as humoral, immunity. In particular, U.S. Pat. No. 5,830,463 demonstrated that yeast which are genetically engineered to express a heterologous antigen can elicit both a cell-mediated and a humoral immune response when administered to a mammal.

There is currently a need for improved vaccines that stimulate T cell-, and particularly cytotoxic T lymphocyte (CTL)-, mediated immunity against cell-associated or endogenous antigens. Targets for these vaccines include cells infected with viruses, intracellular bacteria and parasites, as well as cancers. The initiation of CTL-mediated immunity requires that antigenic peptides be presented in association with major histocompatibility (MHC) class I molecules on the surface of professional antigen presenting cells (APCs) and, in particular, dendritic cells (Dcs) (Ridge et al., *Nature* 393:474–8 (1998)). Dendritic cells are the major antigen presenting cells (APCs) for initiation of immune responses. As DCs are unique in their ability to activate naive $CD4^+$ and $CD8^+$ T cells, they play a crucial role in priming both MHC class II- and class I-restricted, antigen-specific T cell responses (Ridge et al., *Nature* 393:474–8 (1998); Banchereau et al., *Nature* 392:245–52 (1998)). However, exogenously introduced antigens, for example, those found in vaccines consisting of antigenic proteins or killed pathogens, are predominantly processed via the MHC class II pathway for presentation to $CD4^+$ T cells (Moore et al., *Cell* 54:777–85 (1988)). These types of vaccines stimulate potent humoral immunity but are relatively ineffective at stimulating $CD8^+$ CTL. This shortcoming has led to an investigation of vaccine strategies that specifically target DCs to present antigens via MHC class I in addition to class II. DCs have been shown to possess a unique pathway for processing exogenous antigen, especially in particulate form, for presentation by the MHC class I pathway (Rodriguez et al., *Nat Cell Biol* 1:362–368 (1999)). In this regard, various liposome-like, particulate preparations composed of antigenic proteins or peptides with added adjuvants have shown promise at stimulating CTL (Falo et al., *Nat Med* 1:649–53 (1995); O'Hagan, *J Pharm Pharmacol* 50:1–10 (1998)). The particulate nature of these immunostimulatory complexes (ISCOMS) allows them to be readily phagocytosed by DCs that are recruited to the site of vaccination and which become activated by the adjuvant moiety.

Dendritic cell-based cancer vaccines are under intense study as well. Dendritic cells are expanded ex vivo and "loaded" with peptides (derived from suspected tumor antigens) or mixed with the patient's cancer cells (DCs phagocytose the cells and present tumor antigens). However, peptide loading is inefficient and requires knowledge of the particular peptide being used. Phagocytosis of dead tumor cells and debris leads to class II MHC presentation but not class I MHC presentation which is needed for activation of CTL. Therefore, there is a need in the art for improved vaccines, including improved DC vaccines.

SUMMARY OF THE INVENTION

One embodiment of the present invention relates to a therapeutic composition, comprising: (a) a dendritic cell; (b) a yeast vehicle; and, (c) at least one antigen. The dendritic cell has been loaded intracellularly with the yeast vehicle and the at least one antigen. In one aspect, a yeast cell, yeast spheroplast, or other suitable yeast derivative used to prepare the yeast vehicle was transformed with a heterologous nucleic acid molecule encoding the antigen such that the antigen is expressed by the yeast vehicle. In another aspect, prior to loading the yeast vehicle into the dendritic cell, the yeast vehicle was loaded intracellularly with the antigen. In yet another aspect, the antigen was covalently or non-covalently attached to the yeast vehicle prior to loading the yeast vehicle into the dendritic cell. In yet another embodiment, the yeast vehicle and the antigen were associated by mixing prior to or simultaneously with loading into the dendritic cell. In any of the above aspects, the dendritic cell can additionally be loaded with free antigen which can be the same as or different from the antigen used with the yeast vehicle.

The antigen to be used in the therapeutic composition can include, but is not limited to, viral antigens, mammalian cell surface molecules, bacterial antigens, fungal antigens, protozoan antigens, helminth antigens, ectoparasite antigens, and cancer antigens. In one embodiment, the antigen is selected from the group of: HIV-1 gag, HIV-1 env, HIV-1 pol, HIV-1 tat, HIV-1 nef, HbsAG, HbcAg, hepatitis c core antigen, HPV E6 and E7, HSV glycoprotein D, and *Bacillus anthracis* protective antigen. In a preferred embodiment, the composition comprises multiple antigens.

In one embodiment, the composition further comprises at least one biological response modifier.

Preferably, the yeast vehicle is derived from or is a nonpathogenic yeast, although pathogenic yeast can be used. The yeast can be of a genus including, but not limited to, *Saccharomyces, Candida, Cryptococcus, Hansenula, Kluyveromyces, Pichia, Rhodotorula, Schizosaccharomyces* and *Yarrowia*. The yeast vehicle is typically selected from the group of: a whole yeast, a yeast spheroplast, a yeast cytoplast, a yeast ghost, and a subcellular yeast particle.

Another embodiment of the present invention relates to a method to produce a therapeutic composition comprising a dendritic cell loaded with a yeast vehicle and an antigen. The method includes the steps of: (a) forming a yeast vehicle-antigen complex; and, (b) loading the dendritic cell with the yeast vehicle-antigen complex. In one aspect, step (a) is performed by transfecting a yeast vehicle with a nucleic acid molecule encoding the antigen, such that the antigen is expressed by the yeast vehicle. In another aspect, step (a) is performed by loading a yeast vehicle with the antigen by a method selected from the group consisting of: diffusion, active transport, liposome fusion, electroporation, phagocytosis, freeze-thaw cycles and bath sonication. In another aspect, step (a) is performed by mixing together the antigen and the yeast vehicle, prior to or simultaneously with performing step (b). In yet another aspect, step (a) is performed by physically attaching the antigen to a yeast vehicle. Such a step of attaching can be performed by crosslinking the antigen to the yeast vehicle or binding the antigen to a yeast cell wall protein on the yeast vehicle. Step (b) of loading can be accomplished by a method selected from the group of: diffusion, active transport, liposome fusion, electroporation, phagocytosis, and bath sonication.

Yet another embodiment of the present invention relates to a method to elicit an antigen-specific humoral immune response and an antigen-specific cell-mediated immune response in a mammal. The method includes the step of administering to the mammal a therapeutic composition comprising: (a) a dendritic cell; (b) a yeast vehicle; and, (c) at least one antigen. The dendritic cell has been loaded intracellularly with the yeast vehicle and the at least one antigen. Various aspects of the therapeutic composition and method of producing such composition are discussed above. The therapeutic composition is preferably administered by a route selected from the group of: intravenous, intraperitoneal, subcutaneous, intradermal, intranodal, intramuscular, transdermal, inhaled, intranasal, oral, intraocular, intraarticular, intracranial, and intraspinal. In one aspect, the therapeutic composition is administered with a pharmaceutically acceptable excipient.

Yet another embodiment of the present invention relates to a method to elicit an antigen-specific humoral immune response and an antigen-specific cell-mediated immune response in a mammal. The method includes the step of administering to the mammal a therapeutic composition comprising: (a) a yeast vehicle; and, (b) at least one antigen. In this embodiment, the yeast vehicle is not complexed with the antigen. The therapeutic composition is preferably administered by a route selected from the group of: intravenous, intraperitoneal, subcutaneous, intradermal, intranodal, intramuscular, transdermal, inhaled, intranasal, oral, intraocular, intraarticular, intracranial, and intraspinal. In one aspect, the therapeutic composition is administered with a pharmaceutically acceptable excipient.

BRIEF DESCRIPTION OF THE FIGURES

FIG. 2A is a bar graph showing the response of class I MHC-restricted T cells to pulsed dendritic cells.

DETAILED DESCRIPTION OF THE INVENTION

Figure 1A:
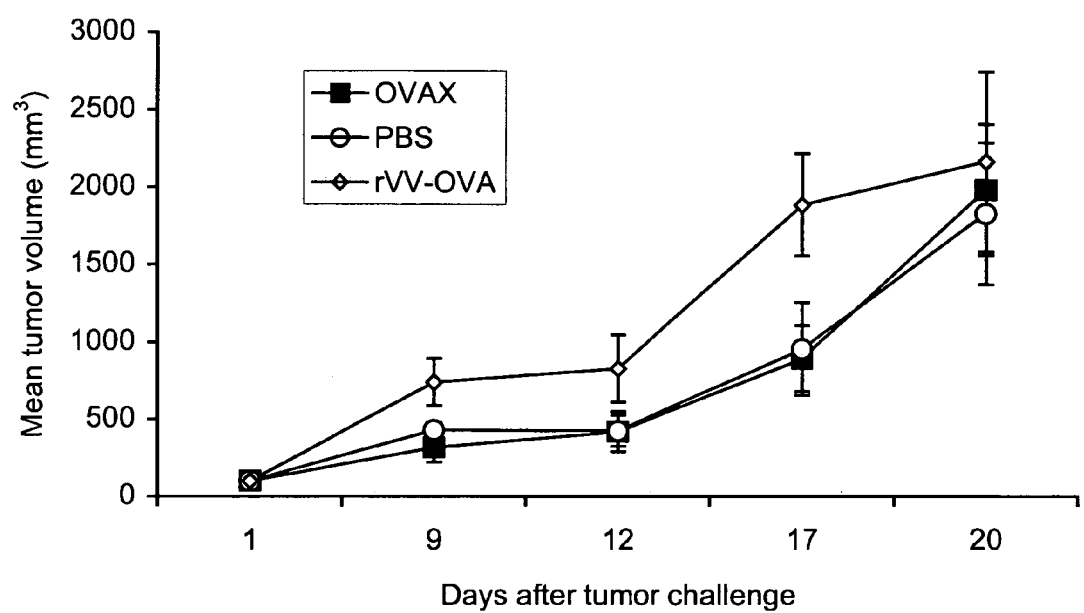
FIG. 1A is a line graph showing growth of EL-4 tumors after vaccination with recombinant yeast expressing ovalbumin (OVAX).

The optimal induction of cell-mediated immunity requires the presentation of antigens by specialized cells of the immune system called dendritic cells (DCs).

Consequently, vaccine strategies that target or activate DCs are the subject of intense research. The present inventors have discovered that yeast vehicles that are associated with antigens, such as by mixing of the yeast and antigen, physical attachment of the antigen to the yeast, internalization of the antigen by the yeast, or recombinant expression of the antigen by the yeast, are potent at inducing antigen-specific, $CD8^+$ T cell responses, including those mediating tumor protection, in vaccinated animals, particularly when the yeast-antigen complexes are loaded into dendritic cells and administered as a novel dendritic cell vaccine. The present inventors further show that yeast-antigen complexes activate dendritic cells to produce IL-12 and to prime MHC class I- and class II-restricted, antigen-specific T cell responses. Yeast-antigen complexes represent a novel vaccine strategy for the induction of broad-based cellular immune responses.

More particularly, the present inventors set out to investigate whether a vaccine strategy that more directly targeted antigen for uptake by DCs might provide a means for inducing potent cell-mediated immune responses, including CTL. Yeast exhibit many of the particulate features of ISCOMS (see Background section), with the added advantage that they naturally possess adjuvant-like properties (Williams et al., *Carbohydr Res* 235:247–57 (1992); Rios-Hernandez et al., *Arch Med Res* 25:179–80 (1994)) and can be easily engineered to express multiple antigens. The present inventors have previously shown that vaccination with whole recombinant *S. cerevisiae* yeast and spheroplasts thereof which are genetically engineered to express heterologous antigens were capable of eliciting CTL-mediated responses and protective immunity in mice. In the present invention, the inventors have made the unexpected discovery that the protective cell-mediated immune responses that have been observed with this approach can be mediated with surprisingly potent results through direct interactions between recombinant yeast and dendritic cells (DCs). Prior to the present invention, there was no indication that dendritic cell that are prepared by loading yeast-antigen complexes would be extraordinarily efficacious as a vaccine, as compared to other vaccine strategies, including administration of a yeast-antigen complex directly to a mammal.

In order for DCs to efficiently present antigens to naive T cells, immature DCs must be activated to mature, as defined by the upregulation of MHC and costimulatory molecules. Mature DCs are then capable of prolonged antigen presentation and the production of cytokines, such as IL-12, that are critical for the induction of cellular immune responses. The present inventors demonstrate herein that yeast provide a powerful activation stimulus to DCs, resulting in up-regulation of co-stimulatory and MHC molecules. These data indicate that the process of internalization of yeast itself, or alternatively, exposure to a yeast-derived factor, matures DCs in a manner similar to that observed when DCs are exposed to microbial activation stimuli such as bacteria or bacterial products (Sallusto et al., *J Exp Med* 182: 389–400 (1995)), including LPS (De Smedt et al., *J Exp Med* 184:1413–24 (1996); Roake et al., *J Exp Med* 181: 2237–47 (1995)). Although the exact mechanism of uptake of yeast by DCs has yet to be determined, one hypothesis is that internalization of yeast may be mediated by DC expression of specific molecular pattern recognition receptors, such as the mannose receptor (Milone & Fitzgerald-Bocarsly, *J Immunol* 161:2391–9 (1998)), or DEC-205 (Jiang et al., *Nature* 375:151–5 (1995)).

The finding reported here that recombinant yeast induce DCs to produce IL-12 without a requirement for $CD4^+$ T cell co-operation is significant from a basic biology viewpoint as well from the viewpoint of vaccine development. A major means of inducing IL-12 secretion from DCs in vitro and in vivo is through the interaction of CD40 ligand expressed on activated $CD4^+$ T cells with CD40 expressed on DCs (Bennett et al., *Nature* 393:478–80 (1998); Schoenberger et al., *Nature* 393:480–3 (1998)). However, other microbial organisms have been shown to bypass this mechanism by directly inducing the secretion of IL-12 from DCs (Sousa et al., *J Exp Med* 186:1819–29 (1997)). The finding that yeast also directly elicit IL-12 production indicates that the therapeutic use of yeast-based vaccines in HIV-1 infection and in certain cancers, in which T helper cell activity has been severely eroded, will be efficacious.

It has been shown that yeast cell wall components, especially beta-1,3-D-glucan and mannan, act as biological response modifiers (Williams et al., *Carbohydr Res* 235: 247–57 (1992); Rios-Hernandez et al., *Arch Med Res* 25:179–80 (1994); Toda et al., *Immunology* 92:111–7 (1997); Shibata et al., *J Immunol* 159:2462–7 (1997)). The present inventors' data demonstrate that yeast act as a potent adjuvant and augment the ability of DCs pulsed with exogenous whole protein antigen to stimulate both MHC class I- and class II-restricted primary T cell responses in vitro. The inventors have shown that pre-incubation of DCs with control yeast (YVEC) together with whole OVA protein increased the ability of DCs to stimulate naive OVA-specific T cells. In fact, OVA protein-pulsed DCs were unable to prime class I restricted T cells at all in the absence of yeast. Yeast acted as an adjuvant in this system despite the fact that the addition of yeast did not measurably increase OVA uptake by DCs; the amount of exogenous $^{14}C$-labeled OVA protein internalized by DCs under these experimental conditions represented approximately 0.1% of the available OVA and was not significantly altered by the addition of yeast (data not shown). This finding indicates that the observed increase in antigen-specific stimulation by DCs exposed to yeast results from either a qualitative change in the ability of DCs to process incorporated antigen via the MHC class I pathway or an increase in the efficiency of antigen presentation. Given that yeast mature DCs and induce IL-12 production, without being bound by theory, the present inventors believe that these biological responses of DCs to yeast may in part account for the observed adjuvanticity of yeast within this system. In support of this theory, DC maturation and IL-12 production have been shown to be associated with increased DC immunogenicity in a number of other systems (Cella et al., *J Exp Med* 184:747–52 (1996); Koch et al., *J Exp Med* 184:741–6 (1996); Sousa et al., *J Exp Med* 186:1819–29 (1997)).

Although yeast clearly exert a potent adjuvant effect on DC-mediated stimulation of both MHC class I- and class II-restricted T cell responses, the efficiency with which recombinant yeast-expressed antigens are processed and presented by DCs cannot be completely accounted for by the adjuvant properties of yeast alone. Recombinant yeast appear to provide antigen to DCs in discrete, concentrated packages that are avidly internalized, thereby effectively increasing the amount of antigen available for processing. Indeed, the process of phagocytosis has been shown to be an extremely efficient means of antigen loading (Inaba et al., *J Exp Med* 188:2163–73 (1998)).

The vaccine and methods of the present invention integrates efficient antigen delivery with extremely effective T cell activation in a powerful vaccine formulation that does not require accessory adjuvant components. The vaccine approach described herein has many attributes that make it an ideal vaccine candidate, including ease of construction, low expense of mass production, biological stability, and safety. No grossly adverse effects of immunization with whole yeast were apparent at the time of the initial vaccination or upon repeated administration in either mice, rabbits, pig-tailed macaques (*Macaca nemestrina*), or immunodeficient CB.17$^{scid}$ mice (unpublished observations). The ability of yeast-antigen complexes to mature DCs into potent APCs while efficiently delivering antigens into both MHC class-I and class-II processing pathways indicates that yeast-based vaccine vectors, particularly as a component of a dendritic cell vaccine, will provide a powerful strategy for the induction of cell-mediated immunity directed against a variety of infectious diseases and cancer targets.

One embodiment of the present invention relates to a therapeutic composition, or vaccine. The composition comprises: (a) a dendritic cell; (b) a yeast vehicle; and, (c) at least one antigen. The dendritic cell has been loaded intracellularly with the yeast vehicle and with at least one antigen to form the therapeutic composition. Also included in the invention is a method to make such a therapeutic composition and a method to use such a composition to elicit an antigen-specific cellular and humoral immune response in a mammal.

Therefore, one component of a therapeutic composition of the present invention is a dendritic cell. According to the present invention, a dendritic cell useful in the present composition can be any dendritic cell as known in the art, which can also be referred to herein as "DC". Dendritic cells are cells of monocyte and lymphocyte lineages, and are known to be the most potent antigen presenting cell (APC) and to stimulate antigen-specific T cell responses. Mature dendritic cells are typically identified as having the following cell surface marker phenotype: MAC3$^-$, CD80$^+$, CD86$^+$, CD40$^{low}$, CD54$^+$, MHC Class I and MHC Class II, and are capable of FITC-dextran uptake. The dendritic cell used in the composition of the present invention is preferably isolated from a patient to which the composition is to be administered (i.e., autologous cells). Dendritic cells can be isolated from the bone marrow or peripheral blood. Such cells can be generated, for example, from peripheral blood monocytes by culture in the presence of granulocyte macrophage colony-stimulating factor, IL-4, and TNFα, for example. Other methods for isolating and generating dendritic cells are known in the art (See, for example, Wilson et al., 1999, *J Immunol* 162: 3070–8; Romani et al., 1994, *J Exp Med* 180: 83–93; Caux et al., 1996, *J Exp Med* 184: 695–706; and Kiertscher et al., 1996, *J Leukoc Biol* 59: 208–18, each of which is incorporated herein by reference in its entirety). A therapeutic composition effective to administer to a patient contains from about $0.5 \times 10^6$ to about $40 \times 10^6$ dendritic cells per single dose per individual patient. Preferably, a therapeutic composition contains from about $1 \times 10^6$ to about $20 \times 10^6$ dendritic cells per single dose per patient, and in another embodiment, from about $1 \times 10^6$ to about $10 \times 10^6$ dendritic cells per single dose per patient. These doses are given for a typical human or other primate. Doses suitable for other animals can be determined by those of skill in the art. For example, for a mouse, a suitable dose is from about $1 \times 10^6$ to about $3 \times 10^6$ per single dose per mouse. Other doses can be determined by the skilled artisan and is well within the ability of those of skill in the art.

A second component of the therapeutic composition of the present invention is a yeast vehicle. According to the present invention, a yeast vehicle is any yeast cell (e.g., a whole or intact cell) or a derivative thereof (see below) that can be used in conjunction with an antigen in a dendritic cell vaccine or as an adjuvant. The yeast vehicle can therefore include, but is not limited to, a live intact yeast microorganism (i.e., a yeast cell having all its components including a cell wall), a killed (dead) intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), or a subcellular yeast particle.

Yeast spheroplasts are typically produced by enzymatic digestion of the yeast cell wall. Such a method is described, for example, in Franzusoff et al., 1991, *Meth. Enzymol.* 194, 662–674, incorporated herein by reference in its entirety. Yeast cytoplasts are typically produced by enucleation of yeast cells. Such a method is described, for example, in Coon, 1978, *Natl. Cancer Inst. Monogr.* 48, 45–55. incorporated herein by reference in its entirety. Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608–3614 and Bussey et al., 1979, *Biochim. Biophys. Acta* 553, 185–196, each of which is incorporated herein by reference in its entirety. A subcellular yeast particle refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast particles is described, for example, in Franzusoff et al., 1991, *Meth. Enzymol.* 194, 662–674.

Any yeast strain can be used to produce a yeast vehicle of the present invention. Yeast are unicellular microorganisms that belong to one of three classes: Ascomycetes, Basidiomycetes and Fungi Imperfecti. While pathogenic yeast strains, or nonpathogenic mutants thereof can be used in accordance with the present invention, nonpathogenic yeast strains are preferred. Preferred genera of yeast strains include *Saccharomyces, Candida, Cryptococcus, Hansenula, Kluyveromyces, Pichia, Rhodotorula, Schizosaccharomyces* and *Yarrowia*, with *Saccharomyces, Candida, Hansenula, Pichia* and *Schizosaccharomyces* being more preferred, and with *Saccharomyces* being particularly preferred. Preferred species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. More preferred yeast species include *S. cerevisiae, C. albicans, H. polymorpha, P. pastoris* and *S. pombe. S. cerevisiae* is particularly preferred due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain.

A preferred yeast vehicle of the present invention is capable of fusing with the cell type to which the yeast vehicle and antigen is being delivered, such as a dendritic cell, thereby effecting particularly efficient delivery of the yeast vehicle, and in many embodiments, the antigen, to the cell type. As used herein, fusion of a yeast vehicle with a targeted cell type refers to the ability of the yeast cell membrane, or particle thereof, to fuse with the membrane of the targeted cell type (e.g., dendritic cell), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. The present inventors have shown that yeast vehicles of the present invention are readily taken up by dendritic cells (as well as other cells, such as macrophages).

Yeast vehicles can be formulated into compositions of the present invention, including preparations to be loaded into a dendritic cell, using a number of techniques known to those skilled in the art. For example, yeast vehicles can be dried by lyophilization or frozen by exposure to liquid nitrogen or dry ice. Formulations comprising yeast vehicles can also be prepared by packing yeast in a cake or a tablet, such as is done for yeast used in baking or brewing operations. In addition, prior to loading into a dendritic cell, or other type of administration with an antigen, yeast vehicles can also be mixed with a pharmaceutically acceptable excipient, such as an isotonic buffer that is tolerated by the host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal,—or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

One component of a therapeutic composition of the present invention includes at least one antigen for vaccinating an animal. The composition can include, one, two, a few, several or a plurality of antigens, as desired. According to the present invention, the term "antigen" can be used interchangeably with the term "immunogen", and is use herein to describe a protein, cellular composition (whole cell, cell lysate or disrupted cells) or organism (whole organism, lysate or disrupted cells) which elicits a humoral and/or cellular immune response (i.e., is antigenic), such that administration of the immunogen to a mammal (e.g., via a dendritic cell vaccine of the present invention) mounts an antigen-specific immune response against the same or similar proteins, cellular compositions or organisms that are encountered within the tissues of the mammal. Therefore, to vaccinate an animal against a particular antigen means that an immune response is elicited against the antigen as a result of administration of the antigen. Vaccination preferably results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of a therapeutic composition of the present invention can be any detectable increase in any facet of the immune response (e.g., cellular response, humoral response, cytokine production), as compared to in the absence of the administration of the vaccine.

According to the present invention, the general use herein of the term "antigen" refers: to any portion of a protein (peptide, partial protein, full-length protein), wherein the protein is naturally occurring or synthetically derived, to a whole cell, cellular lysate, or a portion thereof, or to a microorganism, extract thereof, or other portion thereof, or to a carbohydrate or other molecule, or a portion thereof, wherein the antigen elicits a humoral and/or cellular immune response. An epitope is defined herein as a single antigenic site within a given immunogen that is sufficient to elicit an immune response. Those of skill in the art will recognize that T cell epitopes are different in size and composition from B cell epitopes, and that epitopes presented through the Class I MHC pathway differ from epitopes presented through the Class II MHC pathway. An antigen can be as small as a single epitope, or larger, and can include multiple epitopes. As such, the size of an antigen can be as small as about 5–12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms). In addition, antigens include carbohydrates, such as those expressed on cancer cells, which can be loaded into the yeast. It will be appreciated that in some embodiments (i.e., when the antigen is expressed by the yeast from a recombinant nucleic acid molecule), the antigen is a protein, fusion protein, chimeric protein, or fragment thereof, rather than an entire cell or microorganism. In preferred embodiments, the antigen is selected from the group of a tumor antigen or an antigen of an infectious disease pathogen (i.e., a pathogen antigen). According to the present invention, an antigen suitable for use in the present composition or vaccine can include two or more epitopes from the same antigen, two or more epitopes or antigens from the same cell, tissue or organism, or two or more different epitopes or antigens from different cells, tissues or organisms. Preferably, the antigen is heterologous to the yeast vehicle (i.e., is not protein that is naturally produced by the yeast vehicle).

In one aspect of the invention, the antigen useful in the present composition is an antigen from a pathogen (including the whole pathogen), and particularly, from a pathogen that is associated with (e.g., causes or contributes to) an infectious disease. An antigen from an infectious disease pathogen can include antigens having epitopes that are recognized by T cells, antigens having epitopes that are recognized by B cells, antigens that are exclusively expressed by pathogens, and antigens that are expressed by pathogens and by other cells. Pathogen antigens can include whole cells and the entire pathogen organism, as well as lysates, extracts or other fractions thereof. In some instances, an antigen can include organisms or portions thereof which may not be ordinarily considered to be pathogenic in a mammal, but against which immunization is nonetheless desired. The antigens can include one, two or a plurality of antigens that are representative of the substantially all of the antigens present in the infectious disease pathogen against which the vaccine is to be administered. In other embodiments, antigens from two or more different strains of the same pathogen or from different pathogens can be used to increase the therapeutic efficacy and/or efficiency of the vaccine.

According to the present invention, a pathogen antigen includes, but is not limited to, an antigen that is expressed by a bacterium, a virus, a parasite or a fungus. Preferred pathogen antigens for use in the method of the present invention include antigens which cause a chronic infectious disease in a mammal. In one embodiment, a pathogen antigen for use in the method or composition of the present invention includes an antigen from a virus. Examples of viral antigens to be used in a vaccine of the present invention include, but are not limited to, env, gag, rev, tar, tat, nucleocapsid proteins and reverse transcriptase from immunodeficiency viruses (e.g., HIV, FIV); HBV surface antigen and core antigen; HCV antigens; influenza nucleocapsid proteins; parainfluenza nucleocapsid proteins; human papilloma type 16 E6 and E7 proteins; Epstein-Barr virus LMP-1, LMP-2 and EBNA-2; herpes LAA and glycoprotein D; as well as similar proteins from other viruses. Particularly preferred antigens for use in the present invention include, but are not limited to, HIV-1 gag, HIV-1 env, HIV-1 pol, HIV-1 tat, HIV-1 nef, HbsAG, HbcAg, hepatitis c core antigen, HPV E6 and E7, HSV glycoprotein D, and *Bacillus anthracis* protective antigen.

Tumor antigens useful in the present invention can include a tumor antigen such as a protein, glycoprotein or surface carbohydrates from a tumor cell, an epitope from a tumor antigen, an entire tumor cell, mixtures of tumor cells, and portions thereof (e.g., lysates). In one embodiment, tumor antigens useful in the present invention can be isolated or derived from an autologous tumor sample. An autologous tumor sample is derived from the mammal to whom the therapeutic composition is to be administered. Therefore, such antigens will be present in the cancer against which an immune response is to be elicited. In one aspect, the tumor antigen provided in a vaccine is isolated or derived from at least two, and preferably from a plurality of allogeneic tumor samples of the same histological tumor type. According to the present invention, a plurality of allogeneic tumor samples are tumor samples of the same histological tumor type, isolated from two or more mammals of the same species who differ genetically at least within the major histocompatibility complex (MHC), and typically at other genetic loci. Therefore, if administered together, the plurality of tumor antigens can be representative of the substantially all of the tumor antigens present in any of the individuals from which antigen is derived. This embodiment of the method of the present invention provides a vaccine which compensates for natural variations between individual patients in the expression of tumor antigens from tumors of the same histological tumor type. Therefore, administration of this therapeutic composition is effective to elicit an immune response against a variety of tumor antigens such that the same therapeutic composition can be administered to a variety of different individuals. In some embodiments, antigens from tumors of different histological tumor types can be administered to a mammal, in order to provide a very broad vaccine.

Preferably, the tumor from which the antigen is isolated or derived is any tumor or cancer, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers thereof. Examples of specific cancer antigens to be used in a vaccine of the present invention include but are not limited to, MAGE, PSA, CEA, HER2/neu, MART1, BCR-ab1, and mutant oncogenic forms of p53, ras, myc and RB-1.

Other preferred antigens to include in compositions (vaccines) of the present invention include antigens that are capable of suppressing an undesired, or harmful, immune response, such as is caused, for example, by allergens, autoimmune antigens, inflammatory agents, antigens involved in GVHD, certain cancers, septic shock antigens, and antigens involved in transplantation rejection. Such compounds include, but are not limited to, antihistamines, cyclosporin, corticosteroids, FK506, peptides corresponding to T cell receptors involved in the production of a harmful immune response, Fas ligands (i.e., compounds that bind to the extracellular or the cytosolic domain of cellular Fas receptors, thereby inducing apoptosis), suitable MHC complexes presented in such a way as to effect tolerization or anergy, T cell receptors, and autoimmune antigens, preferably in combination with a biological response modifier capable of enhancing or suppressing cellular and/or humoral immunity.

Other antigens useful in the present invention and combinations of antigens will be apparent to those of skill in the art. The present invention is not restricted to the use of the antigens as described above.

According to the present invention, the yeast vehicle and the antigen are both loaded intracellularly into a dendritic cell to form the therapeutic composition of the present invention. Various forms in which the loading of both components can be accomplished are discussed in detail below. As used herein, the term "loaded" and derivatives thereof refer to the insertion, introduction, or entry of a component (e.g., the yeast vehicle and/or antigen) into a cell (e.g., a dendritic cell). To load a component intracellularly refers to the insertion or introduction of the component to an intracellular compartment of the cell (e.g., through the plasma membrane and at a minimum, into the cytoplasm, a phagosome, a lysosome, or some intracellular space of the cell). To load a component into a cell references any technique by which the component is either forced to enter the cell (e.g., by electroporation) or is placed in an environment (e.g., in contact with or near to a cell) where the component will be substantially likely to enter the cell by some process (e.g., phagocytosis). Loading techniques include, but are not limited to: diffusion, active transport, liposome fusion, electroporation, phagocytosis, and bath sonication. In a preferred embodiment, passive mechanisms for loading a dendritic cell with the yeast vehicle and/or antigen are used, such passive mechanisms including phagocytosis of the yeast vehicle and/or antigen by the dendritic cell.

The yeast vehicle component and the antigen component of the vaccine are typically loaded into the dendritic cell at approximately the same time or simultaneously, although it is possible to load one component into the cell, followed by the other at some time period later. Preferably, the yeast vehicle and antigen are associated with one another prior to loading into the dendritic cell, although this is not necessary in every embodiment. According to the present invention, the term "yeast vehicle-antigen complex" or "yeast-antigen complex" is used generically to describe any association of a yeast vehicle with an antigen. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transformed with a heterologous nucleic acid molecule encoding the antigen such that the antigen is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen.

According to the present invention, an isolated nucleic acid molecule or nucleic acid sequence, is a nucleic acid molecule or sequence that has been removed from its natural milieu. As such, "isolated" does not necessarily reflect the extent to which the nucleic acid molecule has been purified. An isolated nucleic acid molecule useful for transfecting yeast vehicles include DNA, RNA, or derivatives of either DNA or RNA. An isolated nucleic acid molecule can be double stranded or single stranded. An isolated nucleic acid molecule useful in the present invention includes nucleic acid molecules that encode a protein or a fragment thereof, as long as the fragment contains at least one epitope useful in a composition of the present invention.

Nucleic acid molecules transformed into yeast vehicles of the present invention can include nucleic acid sequences encoding one or more proteins, or portions thereof. Such nucleic acid molecules can comprise partial or entire coding regions, regulatory regions, or combinations thereof. One advantage of yeast strains is their ability to carry a number of nucleic acid molecules and of being capable of producing a number of heterologous proteins. A preferred number of antigens to be produced by a yeast vehicle of the present invention is any number of antigens that can be reasonably produced by a yeast vehicle, and typically ranges from at least one to at least about 5, with from about 2 to about 5 compounds being more preferred.

A peptide or protein encoded by a nucleic acid molecule within a yeast vehicle can be a full-length protein, or can be a functionally equivalent protein in which amino acids have been deleted (e.g., a truncated version of the protein), inserted, inverted, substituted and/or derivatized (e.g., acetylated, glycosylated, phosphorylated, tethered by a glycerophosphatidyl inositol (GPI) anchor) such that the modified protein has a biological function substantially similar to that of the natural protein (or which has enhanced or inhibited function as compared to the natural protein, if desired). Modifications can be accomplished by techniques known in the art including, but not limited to, direct modifications to the protein or modifications to the nucleic acid sequence encoding the protein using, for example, classic or recombinant DNA techniques to effect random or targeted mutagenesis. Functionally equivalent proteins can be selected using assays that measure the biological activity of the protein.

Expression of an antigen in a yeast vehicle of the present invention is accomplished using techniques known to those skilled in the art. Briefly, a nucleic acid molecule encoding at least one desired antigen is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens can be on one or more expression vectors operatively linked to one or more transcription control sequences.

In a recombinant molecule of the present invention, nucleic acid molecules are operatively linked to expression vectors containing regulatory sequences such as transcription control sequences, translation control sequences, origins of replication, and other regulatory sequences that are compatible with the yeast cell and that control the expression of nucleic acid molecules. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is able to be expressed when transfected (i.e., transformed, transduced or transfected) into a host cell.

Transcription control sequences, which can control the amount of protein produced, include sequences which control the initiation, elongation, and termination of transcription. Particularly important transcription control sequences are those which control transcription initiation, such as promoter and upstream activation sequences. Any suitable yeast promoter can be used in the present invention and a variety of such promoters are known to those skilled in the art. Preferred promoters for expression in *Saccharomyces cerevisiae* include, but are not limited to, promoters of genes encoding the following yeast proteins: alcohol dehydrogenase I (ADH1) or II (ADH2), phosphoglycerate kinase (PGK), triose phosphate isomerase (TPI), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome $c_1$ (CYC1), Sec7 protein (SEC7) and acid phosphatase (PHO5), with hybrid promoters such as ADH2/GAPDH and CYC1/GAL 10 promoters being more preferred, and the ADH2/GAPDH promoter, which is induced when glucose concentrations in the cell are low (e.g., about 0.1 to about 0.2 percent), being even more preferred. Likewise, a number of upstream activation sequences (UASs), also referred to as enhancers, are known. Preferred upstream activation sequences for expression in *Saccharomyces cerevisiae* include, but are not limited to, the UASs of genes encoding the following proteins: CYC1, ADH2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in *Saccharomyces cerevisiae* include the termination sequences of the α-factor, GAPDH, and CYC1 genes.

Preferred transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and subcellular yeast particles can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast particles containing desired antigens.

Effective conditions for the production of recombinant yeast vehicles and expression of the antigen by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, erlenmeyer flasks, test tubes, microtiter dishes, and petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

In one embodiment of the present invention, as an alternative to expression of an antigen recombinantly in the yeast vehicle, a yeast vehicle is loaded intracellularly with the protein or peptide antigen, or with carbohydrates or other molecules that serve as an antigen.

Subsequently, the yeast vehicle, which now contains the antigen intracellularly, is loaded into the dendritic cell as described above. As used herein, a peptide comprises an amino acid sequence of less than or equal to about 30 amino acids, while a protein comprises an amino acid sequence of more than about 30 amino acids; proteins can be multimeric. A protein or peptide useful as an antigen can be as small as a T cell epitope (i.e., greater than 5 amino acids in length) and any suitable size greater than that which comprises multiple epitopes, protein fragments, full-length proteins, chimeric proteins or fusion proteins. Peptides and proteins can be derivatized either naturally or synthetically; such modifications can include, but are not limited to, glycosylation, phosphorylation, acetylation, myristylation, prenylation, palmitoylation, amidation and/or addition of glycerophosphatidyl inositol. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens after production, but before loading into dendritic cells. Alternatively, intact yeast can be loaded with the antigen, and then spheroplasts, ghosts, cytoplasts, or subcellular particles can be prepared therefrom. Any number of antigens can be loaded into a yeast vehicle in this embodiment, from at least 1, 2, 3, 4 or any whole integer up to hundreds or thousands of antigens, such as would be provided by the loading of a microorganism or portion thereof, for example.

In another embodiment of the present invention, the antigen is physically attached to the yeast vehicle prior to loading the yeast vehicle into the dendritic cell. Physical attachment of the antigen to the yeast vehicle can be accomplished by any method suitable in the art, including, covalent and non-covalent association methods which include, but are not limited to, chemically crosslinking the antigen to the outer surface of the yeast vehicle or biologically linking the antigen to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen are associated with each other by a more passive, non-specific or non-covalent binding mechanism, such as by gently mixing the yeast vehicle and the antigen together in a buffer or other suitable formulation. The mixture can then be loaded into dendritic cells.

In one embodiment, in addition to loading the dendritic cell with a recombinant yeast vehicle, or any other complex or mixture of yeast vehicle and antigen, the dendritic cell can additionally be loaded with free antigen. As used herein, "free antigen" is antigen that is not directly associated with the yeast vehicle (e.g., expressed, attached to, or otherwise mixed with the yeast in a formulation) when it is introduced (loaded) into the dendritic cell. The present inventors have found that the addition of free antigen with a yeast vehicle-antigen complex of the present invention can provide an additional enhancement of the immune response against the antigen. It is noted that the free antigen(s) loaded into the dendritic cell do not need to be the same antigen as is expressed by the yeast vehicle, loaded into the yeast vehicle, or otherwise associated with the yeast vehicle. In this manner, the immune response against a disease pathogen, tumor cell, or other complex antigen source can be enhanced.

In one embodiment of the present invention, a yeast vehicle can also include biological response modifier compounds, or the ability to produce such modifiers (i.e., by transfection with nucleic acid molecules encoding such modifiers). For example, a yeast vehicle can be transfected with or loaded with at least one antigen and at least one biological response modifier compound. Biological response modifiers are compounds that can modulate immune responses. Certain biological response modifiers can stimulate a protective immune response whereas others can suppress a harmful immune response. Certain biological response modifiers preferentially enhance a cell-mediated immune response whereas others preferentially enhance a humoral immune response (i.e., can stimulate an immune response in which there is an increased level of cellular compared to humoral immunity, or vice versa.). There are a number of techniques known to those skilled in the art to measure stimulation or suppression of immune responses, as well as to differentiate cellular immune responses from humoral immune responses.

Suitable biological response modifiers include cytokines, hormones, lipidic derivatives, small molecule drugs and other growth modulators, such as, but not limited to, interleukin 2 (IL-2), interleukin 4 (IL-4), interleukin 10 (IL-10), interleukin 12 (IL-12), interferon gamma (IFN-gamma) insulin-like growth factor I (IGF-I), transforming growth factor beta (TGF-b) steroids, prostaglandins and leukotrienes. The ability of a yeast vehicle to express (i.e., produce), and possibly secrete, IL-2, IL-12 and/or IFN-gamma preferentially enhances cell-mediated immunity, whereas the ability of a yeast vehicle to express, and possibly secrete, IL-4, IL-5 and/or IL-10 preferentially enhances humoral immunity.

Yeast vehicles of the present invention can be associated with wide variety of antigens capable of protecting a mammal from disease, and this ability is enhanced when the yeast vehicle and antigen are loaded into a dendritic cell to form a vaccine of the present invention. Accordingly, the method of use of the therapeutic composition or vaccine of the present invention preferably elicits an immune response in a mammal such that the mammal is protected from a disease that is amenable to elicitation of an immune response, including cancer or an infectious disease. As used herein, the phrase "protected from a disease" refers to reducing the symptoms of the disease; reducing the occurrence of the disease, and/or reducing the severity of the disease. Protecting a mammal can refer to the ability of a therapeutic composition of the present invention, when administered to a mammal, to prevent a disease from occurring and/or to cure or to alleviate disease symptoms, signs or causes. As such, to protect a mammal from a disease includes both preventing disease occurrence (prophylactic treatment or vaccine) and treating a mammal that has a disease or that is experiencing initial symptoms of a disease (therapeutic treatment or a therapeutic vaccine). In particular, protecting a mammal from a disease is accomplished by eliciting an immune response in the mammal by inducing a beneficial or protective immune response which may, in some instances, additionally suppress (e.g., reduce, inhibit or block) an overactive or harmful immune response. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

More specifically, a vaccine as described herein, when administered to a mammal by the method of the present invention, preferably produces a result which can include alleviation of the disease (e.g., reduction of at least one symptom or clinical manifestation of the disease), elimination of the disease, reduction of a tumor or lesion associated with the disease, elimination of a tumor or lesion associated with the disease, prevention or alleviation of a secondary disease resulting from the occurrence of a primary disease (e.g., metastatic cancer resulting from a primary cancer), prevention of the disease, and stimulation of effector cell immunity against the disease.

For example, one embodiment of the present invention is the use of the therapeutic composition as described above to protect a mammal from a disease caused by an infectious agent. An infectious agent can be any agent that can infect a mammal and cause disease. Such disease may develop rapidly or after a long period of time. Suitable infectious agents against which to protect mammals using the vaccine of the present invention include, but are not limited to, viroids, prions, viruses, bacteria, fungi (including yeast), protozoa (e.g., amebas, flagellates and sporozoa), helminths and ectoparasites. It is within the scope of the present invention to protect a mammal against more than one infectious agent. It should also be noted that although some infectious agents have not been definitively classified into one of these groups, such infectious agents are also included in the present invention.

Preferred yeast vehicles are capable of protecting a mammal from infection by infectious agents that damage, for example, the aural, dermal, enteric, immune, neural, oral/dental, reproductive, respiratory and/or urinary systems of animals. Such infectious agents include, but are not limited to, adenoviruses, arena viruses, bunyaviruses, coronaviruses, hepadnaviruses, herpes viruses, myxoviruses, oncogenic viruses, orthomyxoviruses, papovaviruses, paramyxoviruses, parvoviruses, picornaviruses, pox viruses, rabies viruses, reoviruses, rhabdoviruses, rubella viruses, togaviruses, plant viruses, *Aspergillus, Bacillus, Brugia, Candida, Chlamydia, Coccidia, Corynebacteria, Cryptococcus, Dirofilaria, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae* and *Yersinia* as well as other infectious agents that cause opportunistic infections in animals that are immunodeficient or otherwise immunosuppressed. Additional preferred infectious agents include other harmful microorganisms found in brackish water, food contaminants, wounds, and biological weapons.

Preferred viruses from which to protect organisms using yeast vehicles of the present invention include Coxsackie viruses, cytomegaloviruses, Epstein-Barr viruses, flaviviruses, hepatitis viruses, herpes viruses, influenza viruses, measles viruses, mumps viruses, papilloma viruses, parainfluenza viruses, parvoviruses, rabies viruses, respiratory syncytial viruses, retroviruses and varicella viruses.

Retroviruses, herpes viruses, and hepatitis viruses are more preferred, with leukemia, lymphotrophic, sarcoma and lentiviruses being even more preferred, as are other immunodeficiency or tumor viruses. Particularly preferred lymphotrophic viruses from which to protect organisms include T-lymphotrophic viruses, such as human T-cell lymphotrophic viruses (HTLVs, such as HTLV-I and HTLV-II), bovine leukemia viruses (BLVs) and feline leukemia viruses (FLVs). Particularly preferred lentiviruses include human (HIV), simian (SIV), feline (FIV) and canine (CIV) immunodeficiency viruses, with HIV-1 and HIV-2 being even more preferred.

Cancers to be treated or prevented using the method and composition of the present invention include, but are not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, and metastatic cancers thereof. Particularly preferred cancers to treat with a therapeutic composition of the present invention include primary lung cancers and pulmonary metastatic cancers. A therapeutic composition of the present invention is useful for eliciting an immune response in a mammal to treat tumors that can form in such cancers, including malignant and benign tumors. Preferably, expression of the tumor antigen in a tissue of a mammal that has cancer produces a result selected from the group of alleviation of the cancer, reduction of a tumor associated with the cancer, elimination of a tumor associated with the cancer, prevention of metastatic cancer, prevention of the cancer and stimulation of effector cell immunity against the cancer.

Additional diseases from which to protect an animal using a therapeutic composition of the present invention include, but are not limited to, allergies, autoimmune diseases (e.g., diabetes, multiple sclerosis, rheumatoid arthritis), graft versus host disease (GVHD), hematopoietic disorders, immunodeficiency diseases, immunoproliferative diseases, immunosuppressive disorders, inflammatory diseases, rejection of allografts or xenografts, septic shock, other immunological defects and combinations thereof. Many of these diseases can be acute or chronic. Examples of particular diseases from which mammals can be protected using a vaccine of the present invention are disclosed herein. It is to be noted that such examples are intended only as such and do not limit the wide variety of diseases against which appropriately designed vaccines of the present invention can protect mammals.

One embodiment of the present invention relates to a method to produce a therapeutic composition comprising a dendritic cell loaded with a yeast vehicle and an antigen. The method includes the steps of: (a) forming a yeast vehicle-antigen complex; and, (b) loading the dendritic cell with the yeast vehicle-antigen complex. The various components and methods for producing and combining such components have been described in detail above.

Another embodiment of the present invention relates to a method to elicit an antigen-specific humoral immune response and an antigen-specific cell-mediated immune response in a mammal. The method includes the step of administering to the mammal a therapeutic composition comprising: (a) a dendritic cell; (b) a yeast vehicle; and, (c) at least one antigen, wherein the dendritic cell has been loaded intracellularly with the yeast vehicle and the antigen(s). The therapeutic composition, its components, and methods of preparing the same have described in detail above.

One particular advantage of the present invention is that the therapeutic composition does not need to be administrated with an immunopotentiator such as an adjuvant or a carrier, since the yeast vehicle, antigen and dendritic cell combination elicits a potent immune response in the absence of additional adjuvants. This characteristic, however, does not preclude the use of immunopotentiators in compositions of the present invention. As such, in one embodiment, a composition of the present invention can include one or more adjuvants and/or carriers.

Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

Therapeutic compositions of the present invention can also contain one or more pharmaceutically acceptable excipients. As used herein, a pharmaceutically acceptable excipient refers to any substance suitable for delivering a therapeutic composition useful in the method of the present invention to a suitable in vivo or ex vivo site. Preferred pharmaceutically acceptable excipients are capable of maintaining a dendritic cell and or a yeast vehicle in a form that, upon arrival of the dendritic cell or yeast vehicle at a target cell, tissue, or site in the body, the dendritic cell (loaded with a yeast vehicle and antigen) or the yeast vehicle (associated with an antigen), is capable of eliciting an immune response at the target site (noting that the target site can be systemic). Suitable excipients of the present invention include excipients or formularies that transport, but do not specifically target the vaccine to a site (also referred to herein as non-targeting carriers). Examples of pharmaceutically acceptable excipients include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzol alcohol.

The present invention includes the delivery of a composition comprising dendritic cells that have been loaded with a yeast vehicle and antigen to a mammal. Since the dendritic cell used in the composition is isolated from the patient to be treated (autologous cell) or from another source, and is then loaded with a yeast vehicle and antigen to form a therapeutic composition of the present invention in vitro, the entire administration process of the composition is an ex vivo administration protocol. Ex vivo administration refers to performing part of the regulatory step outside of the patient, such as administering a composition of the present invention to a population of cells (dendritic cells) removed from a patient under conditions such that the yeast vehicle and antigen are loaded into the cell, and returning the cells to the patient. The therapeutic composition of the present invention can be returned to a patient, or administered to a patient, by any suitable mode of administration. Such administration can be systemic, mucosal and/or proximal to the location of the target site (e.g., near a tumor). The preferred routes of administration will be apparent to those of skill in the art, depending on the type of condition to be prevented or treated, the antigen used, and/or the target cell population or tissue. Preferred methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. Particularly preferred routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277–11281, 1992, which is incorporated herein by reference in its entirety). Oral delivery can include solids and liquids that can be taken through the mouth, and is useful in the development of mucosal immunity and since compositions comprising yeast vehicles can be easily prepared for oral delivery, for example, as tablets or capsules, as well as being formulated into food and beverage products. Other routes of administration that modulate mucosal immunity are useful in the treatment of viral infections, epithelial cancers, immunosuppressive disorders and other diseases affecting the epithelial region. Such routes include bronchial, intradermal, intramuscular, intranasal, other inhalatory, rectal, subcutaneous, topical, transdermal, vaginal and urethral routes.

According to the present invention, an effective administration protocol (i.e., administering a vaccine or therapeutic composition in an effective manner) comprises suitable dose parameters and modes of administration that result in elicitation of an immune response in a mammal that has a disease or condition, or that is at risk of contracting a disease or condition, preferably so that the mammal is protected from the disease. Effective dose parameters can be determined using methods standard in the art for a particular disease. Such methods include, for example, determination of survival rates, side effects (i.e., toxicity) and progression or regression of disease. In particular, the effectiveness of dose parameters of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of eliciting an antigen-specific immune response in a mammal when administered one or more times over a suitable time period. Doses can vary depending upon the disease or condition being treated. In the treatment of cancer, for example, a suitable single dose can be dependent upon whether the cancer being treated is a primary tumor or a metastatic form of cancer. One of skill in the art can readily determine appropriate single dose sizes for administration based on the size of a mammal and the route of administration.

A suitable single dose of a therapeutic composition or vaccine of the present invention is a dose that is capable of effectively providing dendritic cells that are loaded with a yeast vehicle and an antigen to a given cell type, tissue, or region of the patient body in an amount effective to elicit an antigen-specific immune response, when administered one or more times over a suitable time period. For example, a preferred single dose of a vaccine of the present invention is from about $0.5 \times 10^6$ to about $40 \times 10^6$ dendritic cells per individual per administration. Preferably, a single dose is from about $1 \times 10^6$ to about $20 \times 10^6$ dendritic cells per individual, and more preferably from about $1 \times 10^6$ to about $10 \times 10^6$ dendritic cells per individual. "Boosters" of a therapeutic composition are preferably administered when the immune response against the antigen has waned or as needed to provide an immune response or induce a memory response against a particular antigen or antigen(s). Boosters can be administered from about 2 weeks to several years after the original administration.

It will be obvious to one of skill in the art that the number of doses administered to a mammal is dependent upon the extent of the disease and the response of an individual patient to the treatment. For example, a large tumor may require more doses than a smaller tumor, and a chronic disease may require more doses than an acute disease. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses includes any number required to treat a given disease.

One embodiment of the present invention relates to another method to elicit an antigen-specific humoral immune response and an antigen-specific cell-mediated immune response in a mammal. This method includes administering to the mammal a therapeutic composition comprising: (a) a yeast vehicle; and, (b) at least one antigen, wherein the yeast vehicle is not complexed with the antigen.

The present inventors have found that it is not necessary for an antigen to be recombinantly expressed by a yeast vehicle to be a potent stimulator of an immune response in a mammal. In experiments described herein, an adjuvant effect of yeast on dendritic cell presentation of OVA to MHC class II-restricted, OVA-specific T cells was observed. DCs pulsed with soluble OVA protein stimulated class II-restricted OVA-specific T cells in a dose-dependent manner. The addition of YVEC yeast (yeast transfected with an empty vector without a gene insert, comparable to wild-type yeast) to the DC+OVA combination resulted in greatly enhanced stimulation of MHC class II-restricted T cells. Therefore, it is an embodiment of the present invention to administer a composition directly to a mammal that includes a yeast vehicle and at least one antigen, wherein the antigen is not complexed with the yeast vehicle. In this embodiment, an antigen that is not complexed with a yeast vehicle refers to an antigen that is not recombinantly expressed by the yeast or loaded into the yeast, or physically attached to the yeast, but can include antigen that is mixed with the yeast, as in a formulation, prior to administration to the mammal. The composition can also be administered by first administering one component, and then another, as a separate administration step. Yeast vehicles and antigens, and methods of preparing the same have been described in detail above. Modes of administration are substantially the same as for administration of a dendritic cell vaccine of the present invention. Preferred modes of administration include, but are not limited to, intravenous, intraperitoneal, subcutaneous, intradermal, intranodal, intramuscular, transdermal, inhaled, intranasal, oral, intraocular, intraarticular, intracranial, and intraspinal. In one embodiment, the composition can further include a pharmaceutically acceptable excipient.

In the method of the present invention, vaccines and therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, goats, sheep, cattle, horses and pigs, with humans being particularly preferred.

The following experimental results are provided for purposes of illustration and are not intended to limit the scope of the invention.

EXAMPLES

Molecular and cell biology techniques used in the following examples are known to those skilled in the art and are described, for example, in Sambrook et al., *Molecular Cloning: A Laboratory Manual*, Cold Spring Harbor Labs Press, 1989; and Guthrie et al. (eds.), ibid. Further techniques are described in detail in Stubbs et al., May 2001, *Nature Medicine* 7:625–629, incorporated herein by reference in its entirety.

Yeast vaccines used in many of the following experiments were prepared as follows. Generation and culturing of HIVAX yeast (recombinant *S. cerevisiae* expressing HIV-$1_{SF2}$ envelope glycoprotein (AFY-435) were previously described (Franzusoff et al., *J Biol Chem* 270:3154–9 (1995)). OVAX was generated by transformation of *S. cerevisiae* with the yeast expression vector Yex-Bx (Amrad Biotech) containing the chicken ovalbumin cDNA (a gift from Dr Michael Bevan) under the control of the copper inducible cup1 gene for controlled gene expression. YVEC was generated by transformation with the empty vector containing no gene insert. Yeast were cultured at 25° C. in yeast nitrogen base (YNB) media supplemented with 2.5% glucose to mid-log phase ($OD_{600}$=0.5) when $CuSO_4.5H_2O$ was added to a final concentration of 0.5 mM. Yeast were cultured for a further 16 hours to induce expression of the ovalbumin protein. Yeast were frozen in aliquots of YNB containing 15% glycerol at −70° C. until used. Yeast were washed and heat killed by incubation for 15 min in 56° C. water bath prior to all experiments.

Antigens used in many of the following experiments were prepared as follows. Purified HIV-$1_{LAV}$ gp120 (gp160 devoid of the gp41 fusogen) derived from recombinant *E. coli*, HIV-$1_{SF2}$ gp120 derived from recombinant *S. cerevisiae*, HIV-$1_{SF2}$ gp120 derived from transfected mammalian CHO cells, and Feline leukemia virus (FeLV) gp130 envelope protein derived from recombinant *S. cerevisiae*, were obtained from Chiron Corporation (Emeryville, Calif.) through the AIDS Research and Reference Reagent Program (NIH; Rockville, Md.). Chicken ovalbumin and concanavalin A were purchased from Sigma (St. Louis, Mo.). HPLC purified ovalbumin peptides were obtained >99% pure from the Molecular Resource Center at National Jewish Medical and Research Center, Denver, Colo. Antigens and mitogens were prepared as stock solutions in PBS and were stored at −70° C. until used.

Dendritic cells used in many of the following experiments were isolated and prepared as follows. DCs were cultured from bone marrow of C57BL/6 or BALB/c mice as described with slight modification (Mayordomo et al., *J Exp Med* 183:1357–65 (1996)). Briefly, bone marrow was flushed from the femurs and tibia of mice and red cells lysed with buffered ammonium chloride. Cell suspensions were depleted of B and T cells by incubation with B cell hybridoma supernatants containing monoclonal antibodies specific for murine CD8 (ATCC TIB 105), CD4 (ATCC TIB 207) and B220 (ATCC TIB 146), followed by addition of rabbit complement (Lowtox, Cedarlane/Accurate). Bone marrow at $1\times10^6$ cells/well were cultured in 6 well tissue culture plates containing 3 mls/well RPMI-1640 supplemented with 1000 U/ml mGM-CSF and 1000 U/ml IL-4 R & D Systems, Minneapolis, Minn.). Non-adherent cells were removed on day 2 and fresh media added. Surface phenotype of cells was evaluated on day 5–7 by flow cytometry. ~70% of cultured cells expressed DC phenotype (MAC3−, CD80+, CD86+, CD40$^{low}$, CD54+, H-2K+, I-A$^b$+, and capable of FITC-dextran uptake). Flow data was confirmed by examination of cell cultures microscopically for cells with a dendritic veiled phenotype.

Fluorescent microscopy used in many of the following examples was performed as follows. Yeast were stained for 30 min at a density of $4\times10^6$ yeast/ml in YNB media containing 0.1% MitoTracker Red CMX Ros (Molecular probes, Eugene, Oreg.), washed and heat killed at 56° C. for 15 min. DCs cultured from murine bone marrow were co-incubated for varying periods with stained yeast as indicated. After co-incubation DCs were harvested and surface-stained with FITC conjugated antibodies to murine CD11c or I-A$^b$ following the same procedure as for flow cytometry. Cells were immediately plated onto polylysine-coated cover slips, incubated for 10 min. at 37° C., then fixed and prepared for microscopy as described (Monks et al., *Nature* 385, 83–6 (1997)). Immunofluorescent images were recorded by a digital fluorescence microscopy system controlled by SlideBook software (Intelligent Imaging Innovations, Denver, Colo.) for 3-D image capture, deconvolution and rendering. The images were assembled in Adobe Photoshop (Adobe Systems, San Jose, Calif.).

IL-12 ELISA used in the following experiments were performed as follows. DCs were pulsed with various antigens as indicated following the protocol for DC maturation experiments below. Individual wells were harvested at various time points and supernatant frozen at −80° C. for subsequent ELISA analysis. IL-12 was quantified using Immulon II plates (Dynex Technologies, Chantilly, Va.) and a murine IL-12 ELISA kit (PharMingen, San Diego, Calif.) with a single modification to the manufacturers instructions, which separated the incubations of the biotinylated detection Ab and the streptavidin-HRP conjugate. Plates were read on a Molecular Devices microplate reader (Sunnyvale, Calif.) and data analysis performed using SoftMax sofware (Molecular Devices).

Flow cytometry used in the following examples was performed as follows. All antibodies were obtained from PharMingen (San Diego, Calif.) either biotinylated or directly conjugated to PE, FITC or CyChrome unless otherwise stated. Cells were incubated with antibodies specific for cell surface markers for 30 min, then washed three times. For biotinylated Ab's, a second ten-minute incubation with a streptavidin-conjugated fluorochrome was included followed by three washes before analysis on a Beckton Dickinson FACStar flow cytometer.

Purified naive T cell populations used in the following experiments were prepared as follows. OT-1 and DO 11.10 T-cell receptor transgenic mice aged 6–8 weeks were sacrificed by $CO_2$ inhalation. Spleens and lymph nodes were removed and a single cell suspension obtained by pressing tissue gently through a 70 µM nylon mesh screen (Falcon), followed by 2 passages through a 25 G needle using a 10 ml syringe. Red cells were depleted by lysis with buffered ammonium chloride, and purified lymphocytes passed over nylon wool columns to obtain a T-cell enriched fraction. Specificity of the purified OT-1 T cell population was determined using a PE-conjugated MHC class I tetrameric reagent comprising H-2 Kb in association with the OVA-derived SIINFEKL peptide (SEQ ID NO: 1). Specificity of the DO11.10 purified T cell population was similarly determined using a FITC-conjugated monoclonal Ab (KJ.1) specific for the TCR clonotype.

Tissue culture media used in the following experiments was prepared as follows. With the exception of bone marrow cultures of DC's, all assays were performed in RPMI-1640 (Life Technologies, Rockville, Md.) supplemented with 10% FBS (Hy-Clone); β2-mercaptethanol at $5 \times 10^{-5}$ M (Sigma) and gentamicin-sulphate at 10 µg/ml (Life Technologies). E.G7-OVA were maintained in the presence of 500 µg/ml G4.18 (Genticin; Life Technologies, Rockville, Md. Supernatants from rat spleen cells stimulated for 24 h in the presence of 2.5 mg/ml concanavilin A (Con A) were used as a source of T cell growth factors for mouse T cells (rat CAS).

Infection of cells with recombinant vaccinia virus was performed as follows. $1 \times 10^6$ mouse P815 leukemia cells ($H-2^d$) or EL-4 lymphoma cells ($H-2^b$) were incubated with $1 \times 10^6$ pfu recombinant vaccinia virus expressing b-galactosidase (rVV-lac) or HIV-1$_{SF2}$ gp160 (rVV-gp160-SF2) overnight. Both viruses were generated and propagated using standard protocols. Infected cells were washed three times with TCM prior to use in cytotoxicity assays.

T cell proliferation assays using cells obtained from mice vaccinated with HIVAX were performed as follows. Mice were sacrificed by $CO_2$ inhalation and spleen and mesenteric lymph nodes were harvested under aseptic conditions. Single-cell suspensions were prepared by gently pressing the organs through nylon-mesh screening. B cells and adherent cells were removed from half of the spleen and lymph node cell suspensions by "panning" on petri dishes coated with goat anti-mouse Ig. The T cell enriched spleen and lymph node cells were diluted to $4 \times 10^6$ cells/ml in TCM. Unfractionated, irradiated spleen and lymph node cells from the same mice were subjected to $^{60}Co$ irradiation (3000 R) and were diluted to $4 \times 10^6$ cells/ml in TCM; these cells were used as a source of antigen presenting cells (APC). Enriched T cells and irradiated cells from the same mouse were mixed 1:1 such that the final concentration of each cell type was $2 \times 10^6$/ml. 100 ml of the T cell mixtures were placed in individual wells of 96-well U-bottomed plates which contained antigens or mitogens. Assays were set up in triplicate. On days 3 and 6 plates were pulsed by addition of 1 mCi $^3$HTdR/well in 25 ml TC media. Plates were incubated for a further 16 hours, and $^3$H-thymidine incorporation measured on a Wallac LKB Betaplate 1205 liquid scintillation counter.

The T cell proliferation assays using cells obtained from T cell receptor transgenic mice stimulated by dendritic cells were performed as follows. DCs after 8 days of culture from murine bone marrow were co-incubated overnight in a volume of 1 ml, with varying concentrations of antigen including peptides, whole ovalbumin protein (Sigma), or recombinant yeast at various concentrations as indicated in the text. After overnight incubation, cells were subjected to $^{60}Co$ irradiation (3000 R) and washed in ice-cold Hanks balanced salt solution to remove excess antigen. DC density was adjusted to $1 \times 10^5$/ml in TC media, and ten-fold serial dilutions made to obtain $1 \times 10^4$, $1 \times 10^3$ and $1 \times 10^2$ DC's/ml. 0.1 ml of each DC dilution was combined with 0.1 ml of enriched transgenic T-cells at $1 \times 10^5$/ml, in triplicate, using 96-well U-bottomed tissue culture plates. After 72 hours incubation, plates were pulsed by addition of 1 mCi $^3$HTdR/well in 25 ml TC media, and $^3$H-thymidine incorporation determined as above. All experiments were repeated 3 times. Units are given as counts per minute (CPM) and stimulation index (SI) calculated as: CPM of non-pulsed DC's plus T cells/CPM of antigen-Pulsed DC's plus T cells.

Dendritic cell maturation experiments performed in the following experiments were completed as follows. Bone marrow derived DC cultures in 6 well TC plates were pulsed on day 5, without further disruption, with various antigens as indicated in the text. After a further 48 h incubation, cells were harvested, washed free of excess antigen and flow cytometric analysis performed to determine cell surface expression of known DC-surface maturation markers (CD80, CD86, CD54, CD40, MHC class-I and MHC class-II. Experiments were repeated 5 times.

Quantification of OVA produced by OVAX was performed as follows. OVAX and YVEC were lysed in SDS-PAGE sample buffer together with PMSF to inhibit protein degradation as follows: samples were vortexed vigorously for 90 seconds with 100 µl of glass beads, then boiled for 5 minutes. Proteins were separated on a 6% PAGE gel alongside known amounts of ovalbumin protein standards (Sigma) which were combined with an equivalent quantity of YVEC lysate. Electrophoresed samples were transferred by Western blot over night to a nitrocellulose membrane. Bands were developed by ECF (Bio-Rad) using a primary mouse anti-chicken ovalbumin monoclonal antibody (Accurate), and a secondary, goat anti-mouse alkaline phosphatase antibody (Sigma). Band volume was assessed using ImageQuant on a STORM phosphoimager, followed by regression analysis of the standard curve to quantify ovalbumin produced by each batch of OVAX. Over three separate cultures used in these experiments, the amount of ovalbumin protein made by the yeast was calculated to be approximately 5 nmoles/$OD_{600}$ ($1OD_{600}=1.0\times10^7$ viable yeast) by storm analysis of Western-blot.

Quantification of OVA uptake by DCs was performed as follows. DCs were suspended at $1.0\times10^6$/ml in 1.5 ml of DC media in polypropylene tubes. $^{14}$C-methylated chicken ovalbumin (Sigma, St. Louis, Mo.) was added to a final concentration of 10 mg/ml alone, or in combination with YVEC at 10 yeast per DC. After overnight incubation, DCs were washed in either ice cold HBSS to remove excess antigen, or 150 mM Glycine, pH 4.0 to strip the cell surface of surface bound antigen that had not been internalized. $^{14}$C-OVA incorporation by DCs was then determined by liquid scintillation counter. DCs were shown to incorporate ~10 ng OVA/$10^6$ cells under these experimental conditions.

Cytotoxic T lymphocytes (CTLs) used in the following experiments were generated as follows. In brief, $40\times10^6$ un-fractionated spleen and lymph node cells were placed in flasks containing $2\times10^7$ HIVAX yeast in a total of 10 ml TCM. On day 5, 5% rat CAS was added to all flasks. CTL were harvested by ficoll/hypaque density gradient centrifugation and resuspended in TCM for use.

CTL assays used below were performed as follows. For CTL assays, P815, EL-4, B16, E.G7-OVA, rVV-infected P815 and rVV-B16 melanoma cells were labeled cytoplasmically with 100 µCi $Na_2^{51}CrO_4$ and diluted to $5\times10^4$/ml in TCM. CTL were diluted to $2\times10^7$, $1\times10^7$ and $5\times10^6$ per ml in TCM, 100 µl of CTL and 100 µl of $^{51}$Cr-labeled target cells were mixed together, in triplicate, in 96 well V-bottomed plates yielding final effector-to-target (E:T) ratios of 40:1, 20:1 and 10:1. Cytolysis was determined by release of $^{51}$Cr from the target cells after 4 hr. incubation at 37° C.

Tumorigenicity studies performed in the following experiments were conducted as follows. One million EL-4 or E.G7-OVA lymphoma cells in 100 µl PBS were injected subcutaneously near the vaccination site and on the contralateral flank. Tumor growth was monitored daily. Tumor volume was determined using calipers. Mice were euthanized when tumor volumes exceeded 2 cm$^3$ or at the end of the experiment.

Statistical analyses were performed as follows. For T cell proliferation assays, data was calculated as the mean ±S.D. For CTL assays, data was calculated as mean percent specific cytolysis ±S.D., with spontaneous release of chromium subtracted out. Statistical significance was established using a two-tailed student's t-test comparing the means of experimental vs. control conditions and assuming unequal variances.

Example 1

The following example shows that vaccination of mice with recombinant yeast expressing chicken ovalbumin (OVAX) protects against challenge with E.G7-OVA lymphoma cells. This example also compares a yeast-based vaccine to recombinant vaccinia virus.

The E.G7-OVA mouse tumor model has been employed by many groups to test novel vaccine candidates that induce protective CTL responses (Falo et al., *Nat Med* 1:649–53 (1995); McCabe et al., *Cancer Res* 55:1741–7 (1995); Brossart et al., *J Immunol* 158:3270–6 (1997); Cho et al., *Nat Biotechnol* 18:509–14(2000)). E.G7-OVA are EL-4 lymphoma cells (H-2$^b$) stably transfected with cDNA encoding chicken ovalbumin (Moore et al., *Cell* 54:777–85 (1988)). To test whether recombinant yeast could trigger protective immunity in this tumor model, *Saccharomyces cerevisiae* yeast were engineered to express ovalbumin as a heterologous protein. This yeast preparation was named OVAX.

Figure 1B:
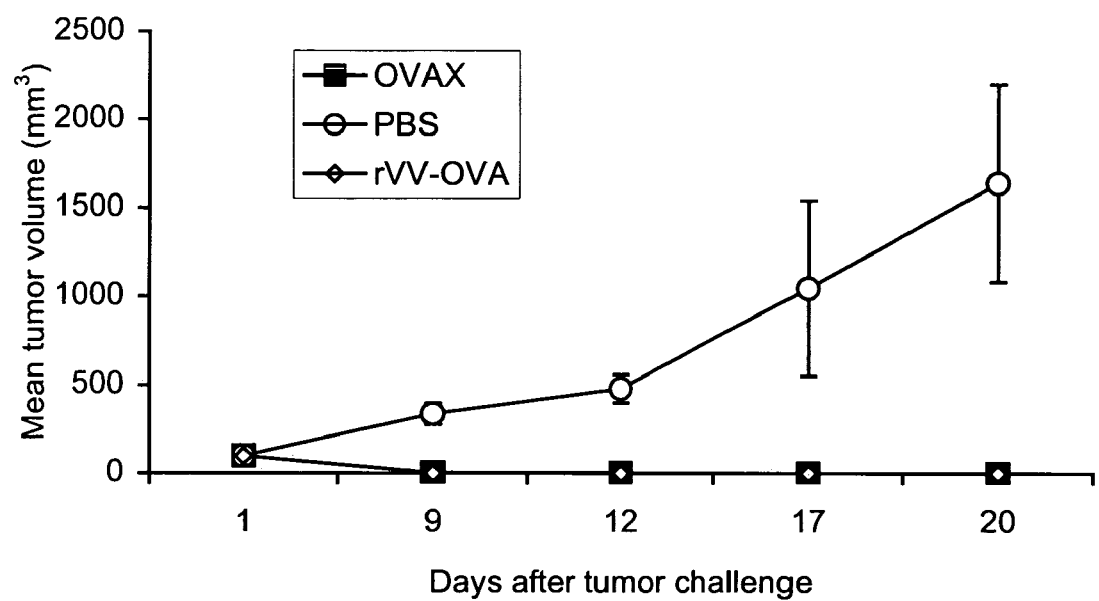
FIG. 1B is a line graph showing growth of E.G7-OVA tumors after vaccination with recombinant yeast expressing ovalbumin (OVAX).

C57B1/6 mice (H-2$^b$) were vaccinated once a week for two weeks with either PBS or $2\times10^7$ whole OVAX yeast. Seven days after the second vaccination, mice were challenged subcutaneously with either EL-4 or E.G7-OVA lymphoma cells implanted contralaterally to the vaccine injection site. As expected, EL-4 lymphomas formed tumors in mock- and OVAX-vaccinated mice that progressed rapidly until their size (>2 cm$^3$) necessitated euthanization (FIG. 1A). In striking contrast, mice vaccinated with OVAX, but not mock-vaccinated animals, were protected from E.G7-OVA tumor formation (FIG. 1B). These results demonstrated that a whole recombinant yeast-based vaccine formulation was capable of eliciting systemic, antigen-specific, protective immunity.

Example 2

The following example demonstrates that CD8 T cells are required for protection against tumor formation induced by OVAX. This particular experiment also showed that OVAX induces anti-OVA antibody.

Figure 1C:
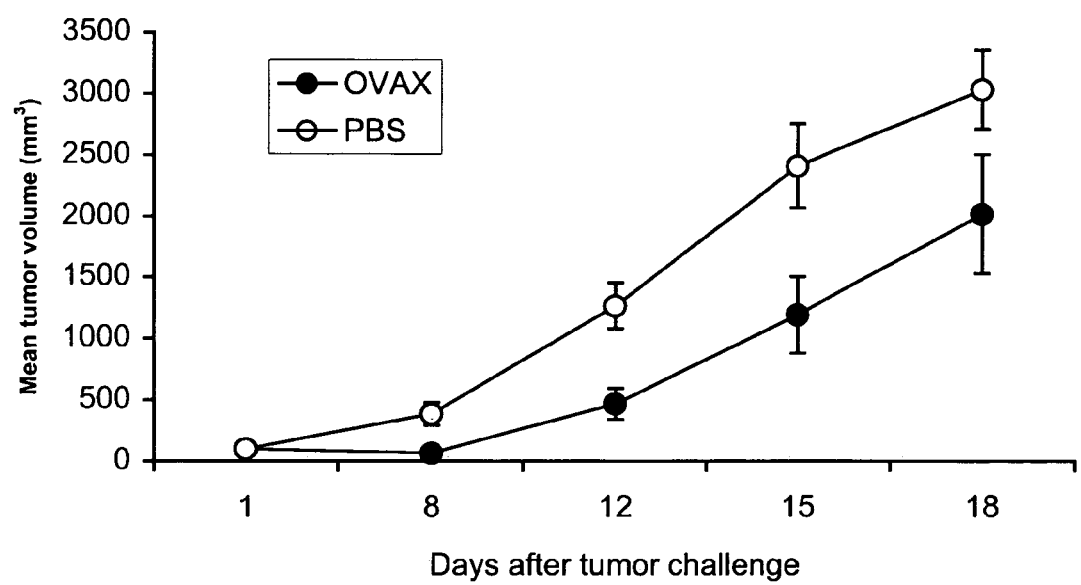
FIG. 1C is a line graph showing growth of E.G7-OVA tumors in $CD8^{-/-}$ mice after vaccination with recombinant yeast expressing ovalbumin (OVAX).

To assess the role of CD8$^+$ CTL function for OVAX-mediated vaccine tumor protection, the study was reproduced in CD8-deficient C57B1/6-Cd8a$^{tm1Mak}$ (CD8$^{-/-}$) transgenic knockout mice. As shown in FIG. 1c, E.G7-OVA tumors progressed similarly in OVAX- or mock-immunized CD8$^{-/-}$ mice, although these mice produced antibodies against OVA (data not shown). These results strongly suggest that the protective immunity elicited by the recombinant yeast vaccine in this tumor model was dependent on CD8$^+$ T cell function.

Example 3

Figure 1D:
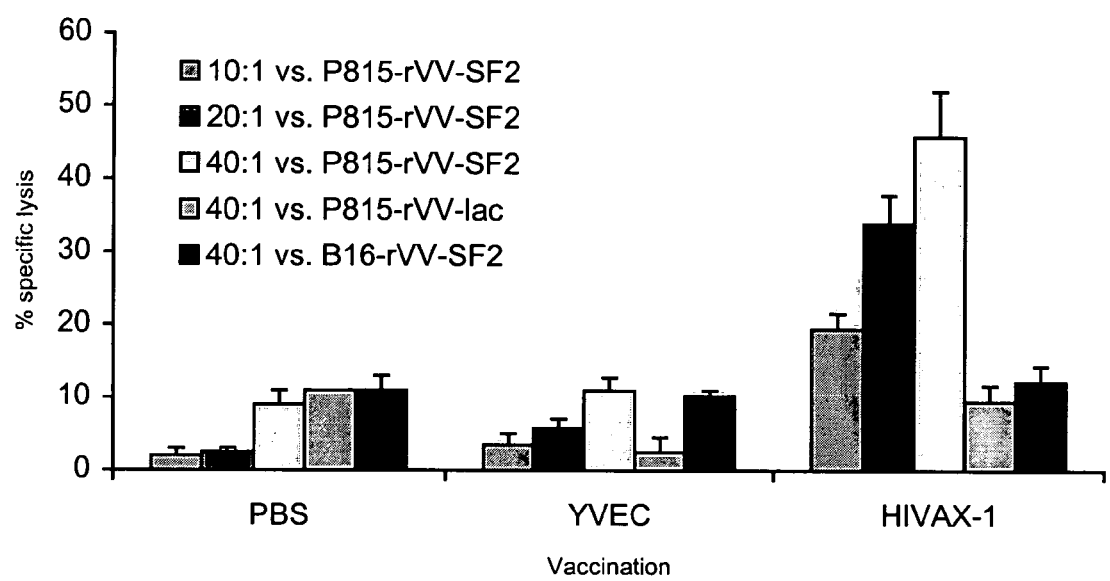
FIG. 1D is a bar graph showing specific lysis of virally infected cells that are producing the antigen by CTLs after vaccination with recombinant yeast expressing HIV gp160 envelope protein (HIVAX).

The following example (FIG. 1D) shows that vaccination of mice with recombinant yeast expressing HIV gp160 envelope protein induce antigen-specific CTL that are capable of killing virally infected cells that are producing the antigen.

In brief, BALB/c mice were injected with $2\times10^7$ HIVAX-1 yeast, $2\times10^7$ YVEC yeast or PBS on days 0, 7 and 14. Mice were sacrificed on day 35 and CTL were restimulated in vitro in the presence of $1\times10^6$ heat-killed HIVAX-1 yeast. 5% CAS was added on day 5. CTL were assayed on the indicated target cells. Results are presented as % specific lysis +/−S.D. for triplicate determinations.

Figure 1E:
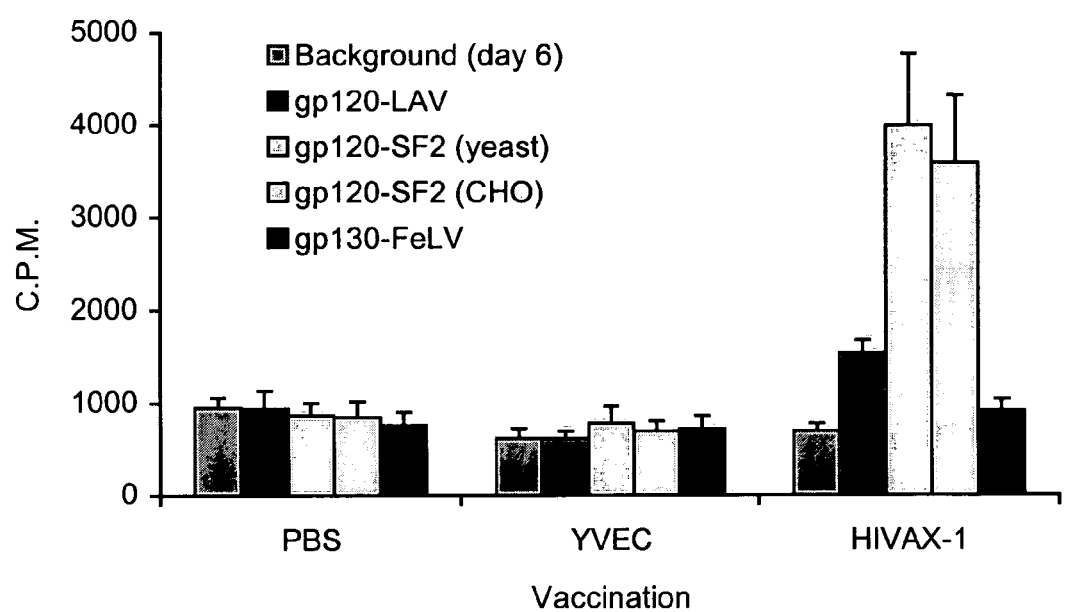
FIG. 1E is a bar graph showing T cell proliferation in response to envelope antigens after vaccination with recombinant yeast expressing HIV gp160 envelope protein (HIVAX).

FIGS. 1Ea and 1Eb show that vaccination of mice with recombinant yeast expressing HIV gp160 envelope protein induce antigen-specific T helper cell that are capable of proliferating in response to envelope antigens.

In brief, BALB/c mice were injected with $2\times10^7$ HIVAX-1 yeast, $2\times10^7$ YVEC yeast or PBS on days 0, 7 and 14. Mice were sacrificed on day 35 and spleen and lymph node T cells were restimulated in vitro in the presence of 1 µg/ml of the indicated antigen. Proliferation was determined by pulsing the cultures with $^3$HTdR on day 6 and harvesting on day 7. Results are presented as C.P.M. +/−S.D. for triplicate determinations.

Example 4

The following example shows that yeast are avidly phagocytosed by dendritic cells, that yeast associated antigens are efficiently processed by dendritic cells into the class I MHC pathway to stimulate CD8 T cells, and that yeast associated antigens are also efficiently processed by dendritic cells into the class II MHC pathway to stimulate CD4 T cells.

The similarity of the yeast-based vaccine to ISCOMs in terms of stimulation of protective CD8$^+$ T cells in vivo prompted an evaluation of the interaction between yeast and dendritic cells in vitro. To determine whether yeast were efficiently phagocytosed by DCs, bone marrow-derived DCs were incubated with control yeast (YVEC) labeled with the fluorescent dye MitoTracker Red. Yeast were internalized within DC by 4 h (data not shown) and appeared fragmented by 24 h (data not shown). Under these experimental conditions, ~90% of available yeast were internalized by DCs in a 24 hour period. A concomitant decrease in red fluorescence intensity was observed as yeast were degraded, and internalized yeast were no longer detected by 72 h (data not shown).

To determine if DCs that had internalized yeast could present yeast-associated antigens via class-I MHC and prime antigen-specific T cells, DCs derived from C57B1/6 mice (H-2b) were incubated with OVAX yeast for 24 h and used to stimulate a naive population of CD8$^+$ T cells derived from OT-1 Tg mice. OT-1 Tg mice are transgenic for an α/β T cell antigen receptor that recognizes the $OVA_{257-264}$ peptide (SIINFEKL; SEQ ID NO: 1) presented in the context of H-2K$^{b12}$. DCs pulsed with YVEC yeast served as negative controls whereas DCs pulsed with SIINFEKL served as positive controls. As shown in FIG. 2A, DCs pulsed with OVAX, but not YVEC yeast, potently induced proliferation of OT-1 Tg T cells. Stimulation occurred in a dose-dependent fashion in that increasing the OVAX yeast to DC ratio resulted in increased antigen-specific T cell proliferation. Presentation of yeast-derived, MHC class-I restricted OVA epitopes appeared to be highly efficient in that the proliferation observed using OVAX estimated to contain ~0.01 nM OVA by quantitative Western analysis (OVAX 20:1; S.I.=359), was similar to that observed with DCs pulsed with an apparently saturating amount of SIINFEKL peptide (1 μM).

Figure 2B:
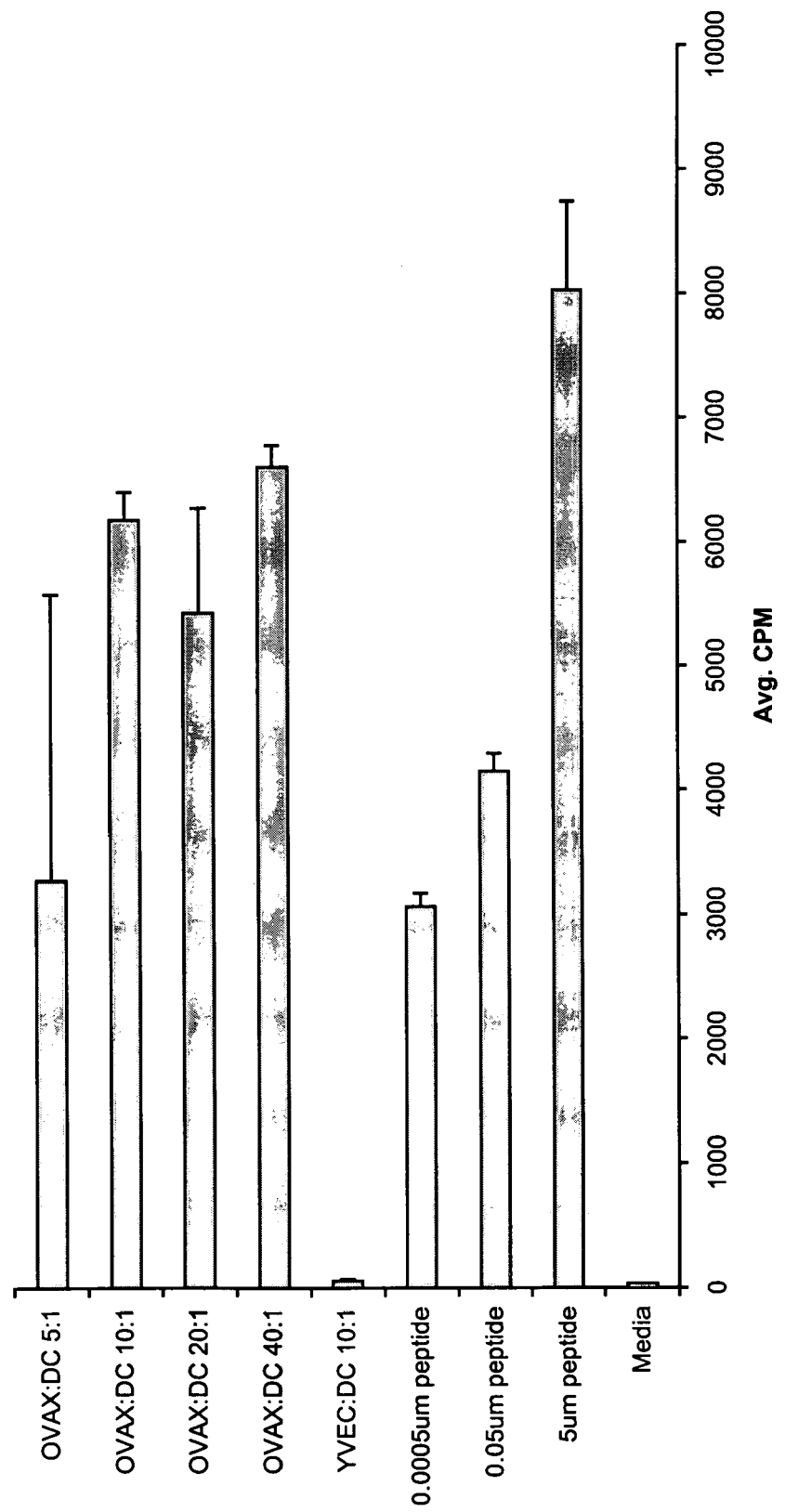
FIG. 2B is a bar graph showing the response of class II MHC-restricted T cells to pulsed dendritic cells.

To ascertain whether yeast-associated proteins were also presented via MHC class-II, the experiments described above were repeated using DCs derived from BALB/c mice and naive CD4$^+$ antigen-specific T cells derived from DO-11.10 Tg mice. DO-11.10 Tg mice are transgenic for an α/β T cell antigen receptor that recognizes $OVA_{323-339}$ peptide presented in the context of I-A$^{d13}$. As shown in FIG. 2B, OVAX-pulsed DCs were highly efficient at stimulating DO-11.10 Tg T cells to proliferate in an antigen-specific fashion. Responses obtained with OVAX-pulsed DCs using as few as 5 yeast per DC (~0.0025 nM OVA) were roughly equivalent to the maximum response obtained with a saturating concentration of cognate peptide (5 mM).

Example 5

The following example shows that yeast stimulate mouse dendritic cells to upregulate costimulatory (CD80, CD86, CD40), adhesion (ICAM-1) and MHC class I and class II molecules, that yeast induce dendritic cells to produce and secrete IL-12, that yeast prime dendritic cells such that they become able to process exogenous antigens into the class I MHC pathway to stimulate CD8 T cells, and that yeast prime dendritic cells such that they become able to process exogenous antigens more efficiently into the class II MHC pathway to stimulate CD4 T cells.

In order for DCs to efficiently present antigens to naive T cells, immature DCs must be activated to mature, as defined by the upregulation of MHC and costimulatory molecules[2]. Mature DCs are then capable of prolonged antigen presentation and the production of cytokines, such as IL-12, that are critical for the induction of cellular immune responses (Cella et al., *J Exp Med* 184:747–52 (1996); Koch et al., *J Exp Med* 184:741–6 (1996)). To determine whether the interaction with yeast resulted in a mature DC phenotype, immature DCs were incubated for 48–72 h alone or with yeast.

Figure 3A:
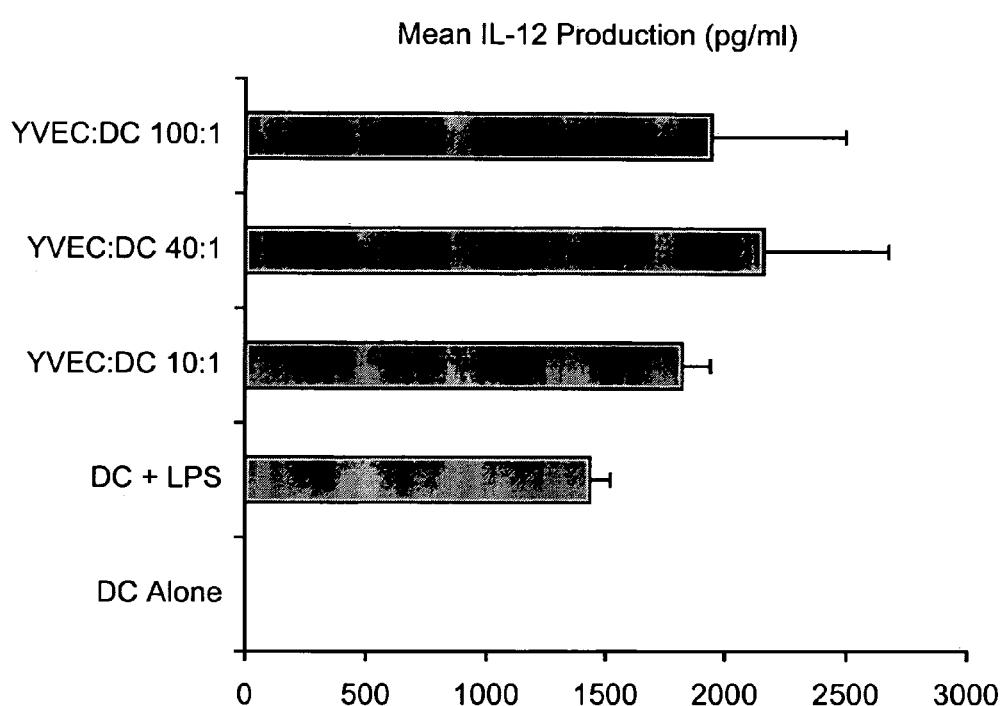
FIG. 3A is a bar graph showing IL-12 production by dendritic cells pulsed with yeast vehicles.

Uptake of yeast by DCs increased surface expression of the co-stimulatory molecules CD40, CD80 and CD86, MHC class II, and the adhesion molecule ICAM (data not shown), to levels comparable to that induced by exposure to bacterial lipopolysaccharide (LPS), a potent DC maturation factor (De Smedt et al., *J Exp Med* 184:1413–24 (1996); Roake et al., *J Exp Med* 181:2237–47 (1995)). As further evidence of yeast-induced activation, DCs pulsed with yeast produced significant amounts of IL-12 that peaked 48 h after stimulation and rivaled that induced by exposure to LPS (FIG. 3A).

Figure 3B:
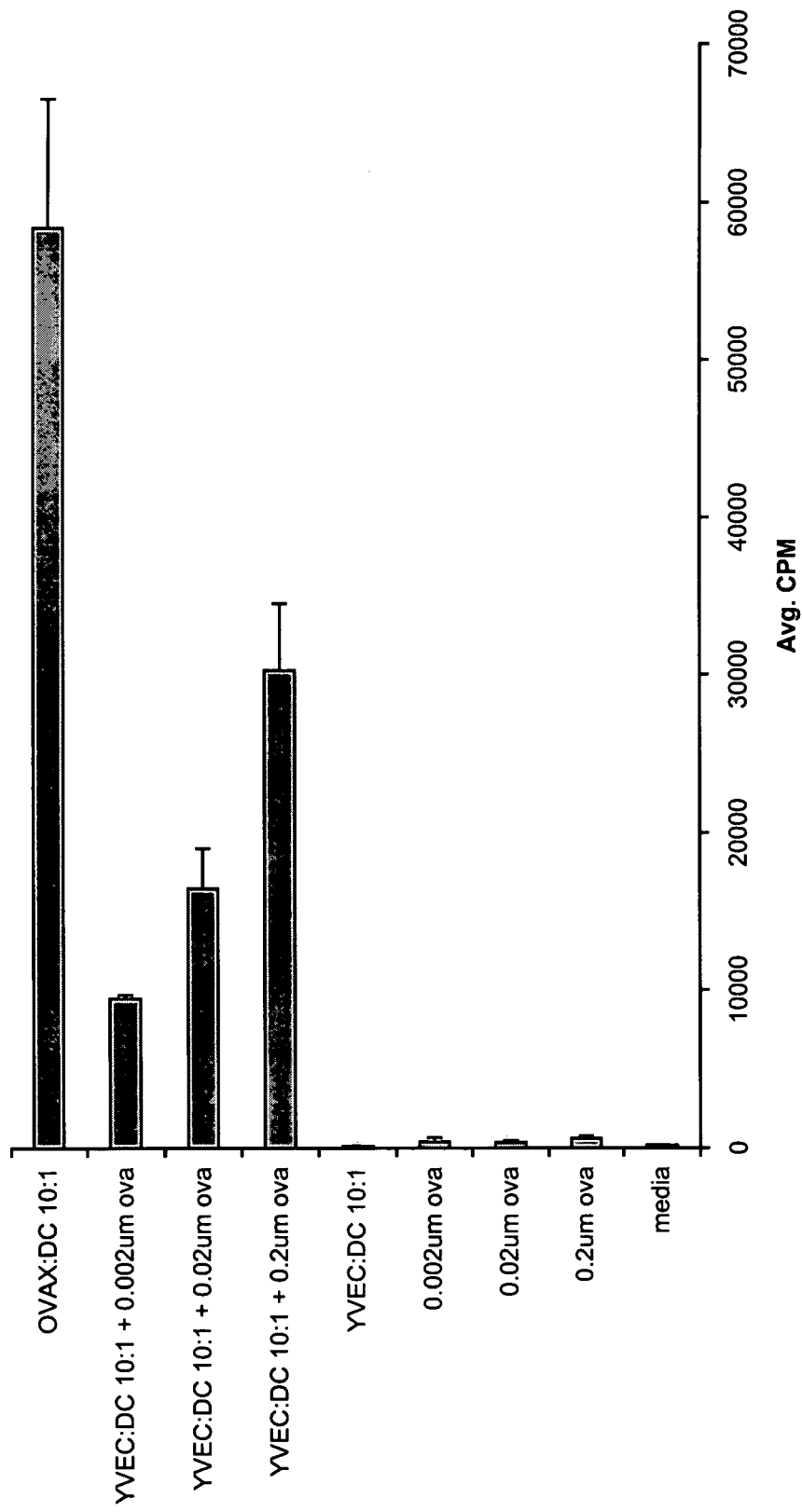
FIG. 3B is a bar graph showing the response of class I MHC-restricted T cells to pulsed dendritic cells.

The observed effect of yeast on DC maturation prompted an investigation into the impact of yeast on the efficiency with which DCs present exogenous ovalbumin (OVA) to naive MHC class I and class II-restricted OVA-specific T cells. C57B1/6- or BALB/c-derived DCs were co-incubated overnight with either OVAX (10 OVAX per DC), graded amounts of whole OVA protein, or combinations of OVA together with YVEC (10 YVEC per DC). The pulsed DCs were irradiated and combined with naive OT-1 or DO 11.10 Tg T cells in a lymphocyte proliferation assay as described above. Very little MHC class I restricted T cell stimulation was obtained from DCs pulsed with exogenous soluble OVA antigen alone (FIG. 3B). Remarkably, combining YVEC with exogenous OVA resulted in a fifty-fold increase in class I-restricted antigen-specific T cell stimulation as compared to exogenous OVA alone (SI=3.4 with 0.2 μM OVA vs. SI=170 with 0.2 μM OVA+YVEC). Despite the increase in OVA-specific T cell stimulation associated with the addition of YVEC, the responses obtained with DCs pulsed with OVAX were greater still. On the basis of per molar antigen, DCs pulsed with OVAX (containing ~0.005 nM OVA at 10 OVAX per DC) yielded twice the stimulation obtained with YVEC plus 0.2 μM OVA.

Figure 3C:
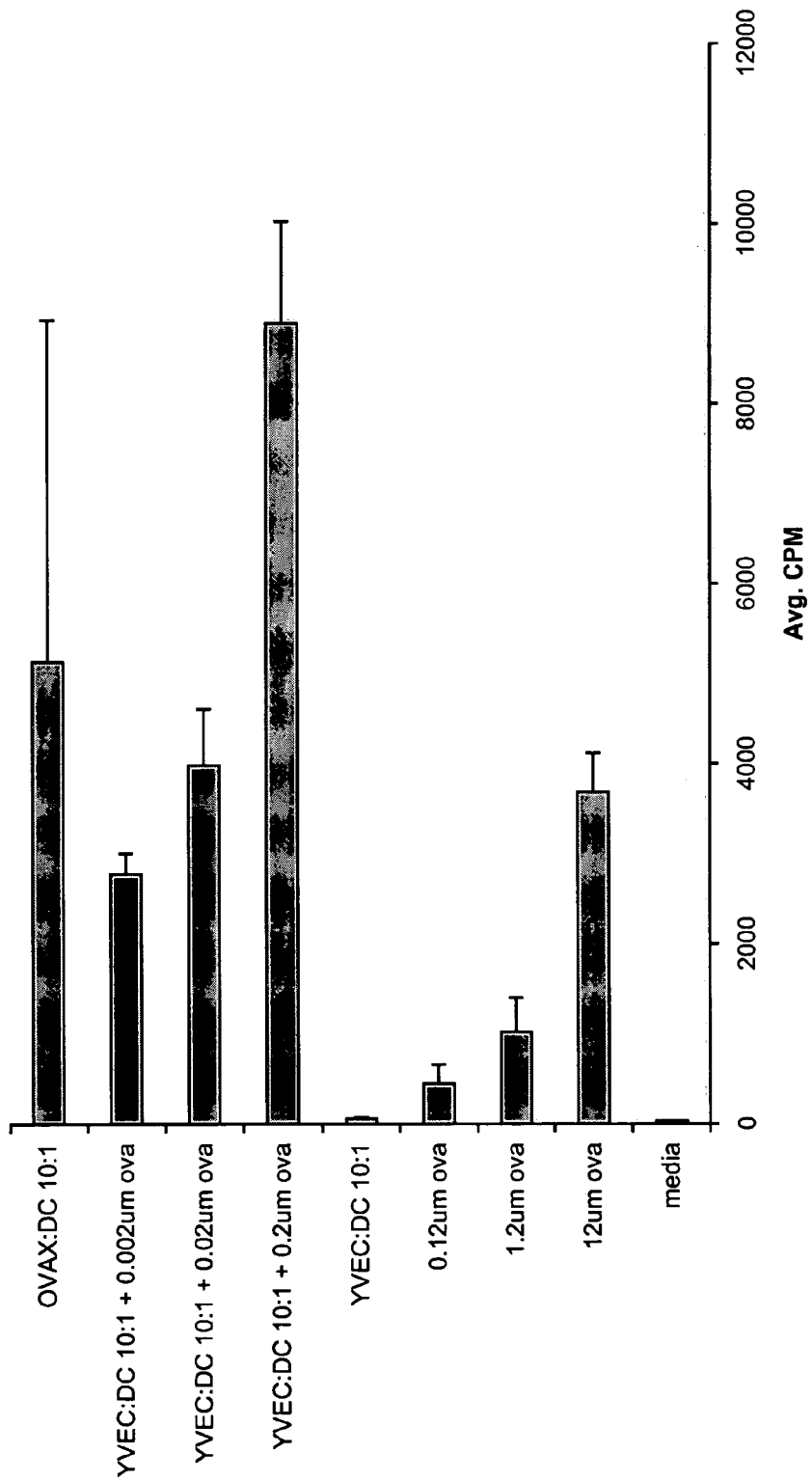
FIG. 3C is a bar graph showing the response of class II MHC-restricted T cells to pulsed dendritic cells.

An adjuvant effect of yeast on DC presentation of OVA to MHC class II-restricted, OVA-specific T cells was also observed (FIG. 3C). DCs pulsed with soluble OVA protein stimulated class II-restricted OVA-specific T cells in a dose-dependent manner. As demonstrated in the MHC class I system, the addition of YVEC yeast to the DC+OVA combination resulted in greatly enhanced stimulation of MHC class II-restricted T cells. Also, as in the class I system, OVAX-pulsed DCs stimulated class II-restricted T cells more efficiently on a per molar antigen basis than did the YVEC+OVA combination. In this representative experiment, proliferation induced by DCs pulsed with YVEC plus 12 μM OVA was comparable to that obtained with ten OVAX per DC, calculated to contain 0.005 nM OVA.

Example 6

The following example demonstrates T cell cytotoxic and proliferative responses elicited in mice vaccinated with HIVAX.

The ability of OVAX yeast to prime naive T cells in vitro and to induce CD8$^+$ T lymphocyte-dependent protective immunity in vivo prompted an investigation as to whether yeast engineered to express a clinically relevant antigen, in this case, the HIV-1$_{SF2}$ gp160 envelope protein (Franzusoff et al., *J Biol Chem* 270:3154–9 (1995)) (HIVAX), could also elicit CTL activity. In brief, BALB/c mice (H-2$^d$) were vaccinated once a week for three weeks with HIVAX, YVEC or PBS. Spleen and lymph node cells isolated from vaccinated mice were stimulated in vitro in the presence of HIVAX and assayed seven days thereafter on six target cell populations: P815 leukemia cells; P815 infected with recombinant vaccinia virus encoding β-galactosidase (rVV-lac); P815 infected with recombinant vaccinia virus encoding HIV-1$_{SF2}$ gp160 (rVV-gp160-SF2); B16 melanoma cells; B16 infected with rVV-lac; and B16 infected with rVV-gp160-SF2. CTL generated from mice that were vaccinated with HIVAX, but not with PBS or YVEC, were able to efficiently kill target cells expressing gp160-SF2 (data not shown). Killing was antigen specific and MHC-restricted; whereas H-2$^d$-bearing P815 cells infected with rVV-gp160-SF2 were killed by the BALB/c (H-2d)-derived CTL, rVV-lac-infected P815 and rVV-gp160-SF2-infected B16 melanoma cells (H-2$^b$) were not (data not shown).

Given that antigen-specific, MHC-restricted CTL activity was observed in HIVAX-vaccinated mice, studies were initiated to determine whether the yeast vaccine might also stimulate activation of antigen-specific helper T lymphocytes. T cells isolated from spleen and mesenteric lymph nodes of HIVAX-, but not mock- or YVEC-vaccinated, mice responded to highly purified, recombinant-derived HIV-1$_{SF2}$-gp120 envelope protein (gp160 devoid of the gp41 fusogen; data not shown). Statistically significant responses were observed as early as day 3, typically reaching a value of eight to ten times over background on day 6. It is important to note that the response was similar regardless of whether the purified HIV-1$_{SF2}$-gp120 was derived from recombinant *Saccharomyces cerevisiae* (yeast) or mammalian cells (CHO). This strongly suggested that the T cells were responding to the HIV envelope protein rather than some contaminating yeast protein in the gp120 preparation. Antigen-specificity was further supported by the observation that the T cells did not respond to yeast-derived Feline leukemia virus gp130 envelope protein.

Example 7

The following example demonstrates that dendritic cells that have engulfed recombinant yeast can be as used a vaccine to induce protective immunity against tumor cells expressing the yeast-encoded antigen, and that such vaccines induce antibodies in vivo.

Figure 4A:
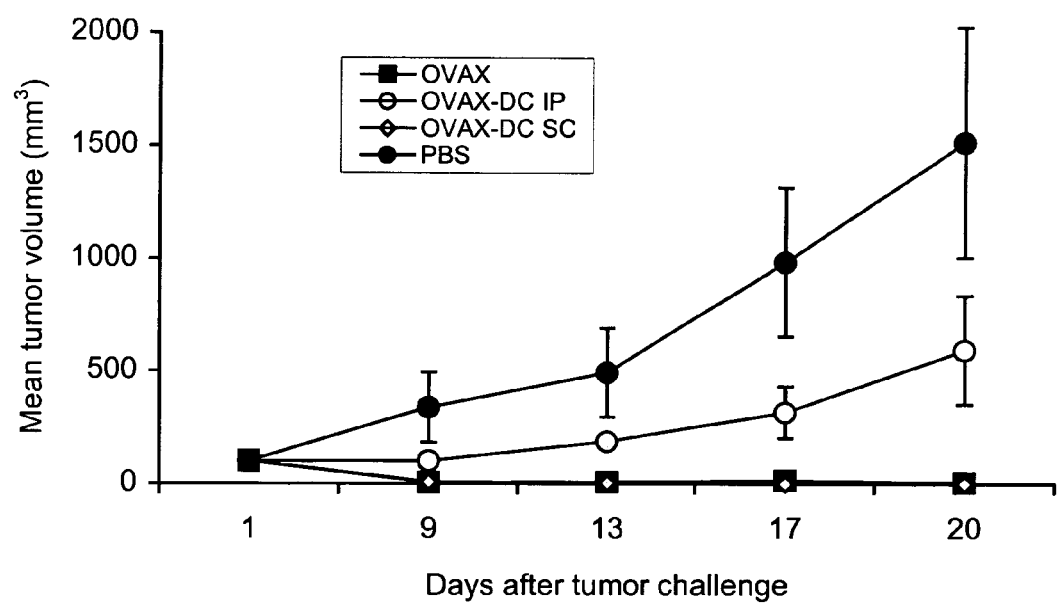
FIG. 4A is a line graph showing EG.7-OVA tumor growth after vaccination with dendritic cells loaded with yeast vehicle and ovalbumin.
Figure 4B:
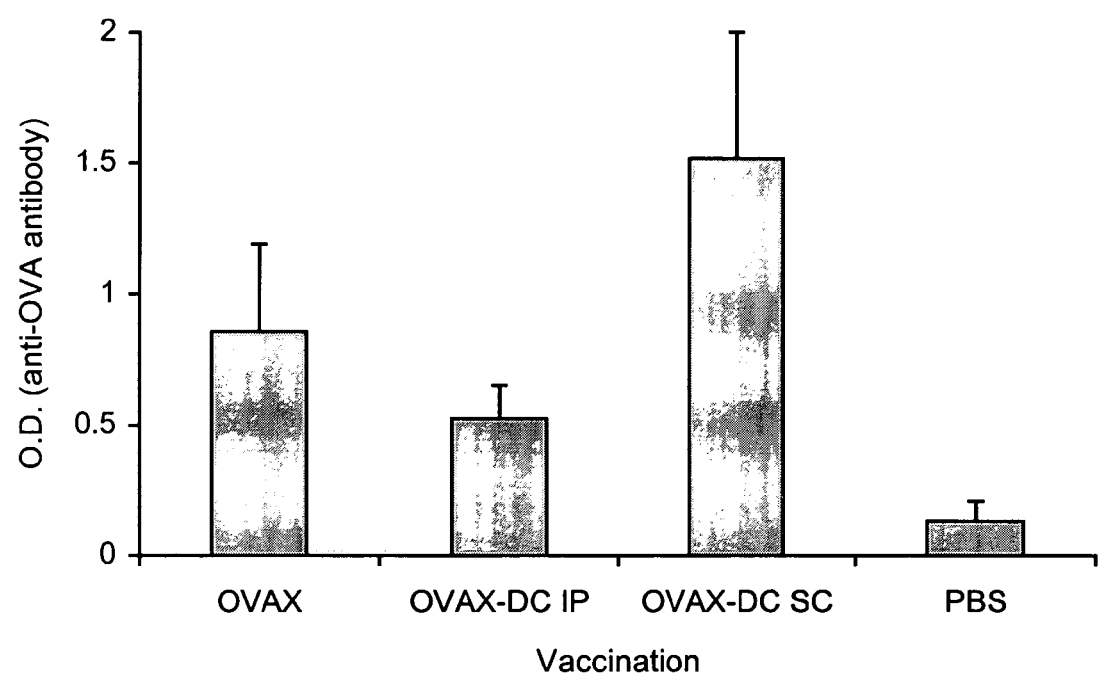
FIG. 4B is a line graph showing antibodies against ovalbumin after vaccination with dendritic cells loaded with yeast vehicle and ovalbumin.

In brief, mice were injected (d0 & d7) with 2×10$^7$ live OVAX yeast, PBS or with 4×10$^5$ bone marrow-derived dendritic cells (7 days in the presence of GM-CSF+IL-4) that had been pulsed with live OVAX yeast (OVAX:DC=10:1) for 24 hr. On day 14, mice were challenged with EL-4 lymphoma cells or E.G7-OVA lymphoma cells. Tumor growth was measured on the indicated day. FIG. 4A shows that dendritic cells that have engulfed recombinant yeast induce protective immunity against cells expressing the yeast-encoded antigen in vivo. FIG. 4B shows that the dendritic cells that have engulfed recombinant yeast induce antibodies in vivo. The antibody production induced by the dendritic cell vaccine (OVAX-DC) administered subcutaneously was superior to the recombinant yeast vaccine (OVAX).

Example 8

The following example demonstrates that yeast can provide an adjuvant effect in vivo allowing for the induction of protective immunity by an exogenously introduced antigen.

Figure 5:
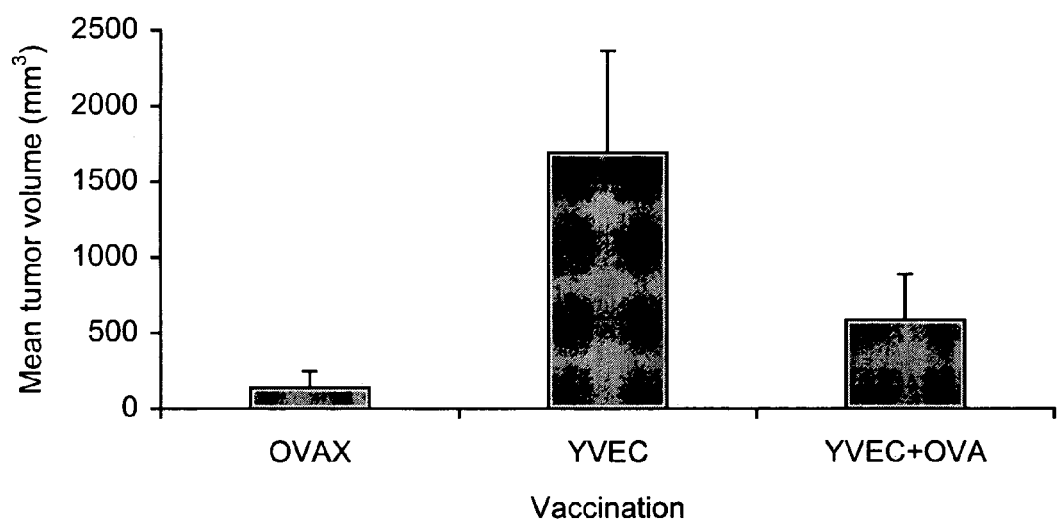
FIG. 5 is a bar graph showing B16-OVA tumor growth after vaccination with OVAX, YVEC or YVEC and ovalbumin.

In brief, 6 week old female C57B1/6 mice were vaccinated sub-cutaneously on days 0 and 7 with 2×10$^7$ live OVAX yeast, 2×10$^7$ live YVEC yeast or 2×10$^7$ live YVEC yeast +50 µg OVA. Mice were challenged with 1×10$^5$ B16-ova cells on day 14. Tumor growth was measured on day 20. FIG. 5 shows that mice administered with OVAX show significant reduction in tumor growth as compared to the YVEC control. Notably, the combination of the yeast with free ovalbumin also reduced tumor growth significantly as compared to yeast alone, although it was not as effective as the OVAX treatment.

Example 9

The following example shows that vaccination of mice with recombinant yeast induce antigen-specific T helper cell that are capable of proliferating in response to yeast antigens. These data also show that non-vaccinated mice do not have pre-existing proliferative responses to yeast.

Figure 6A:
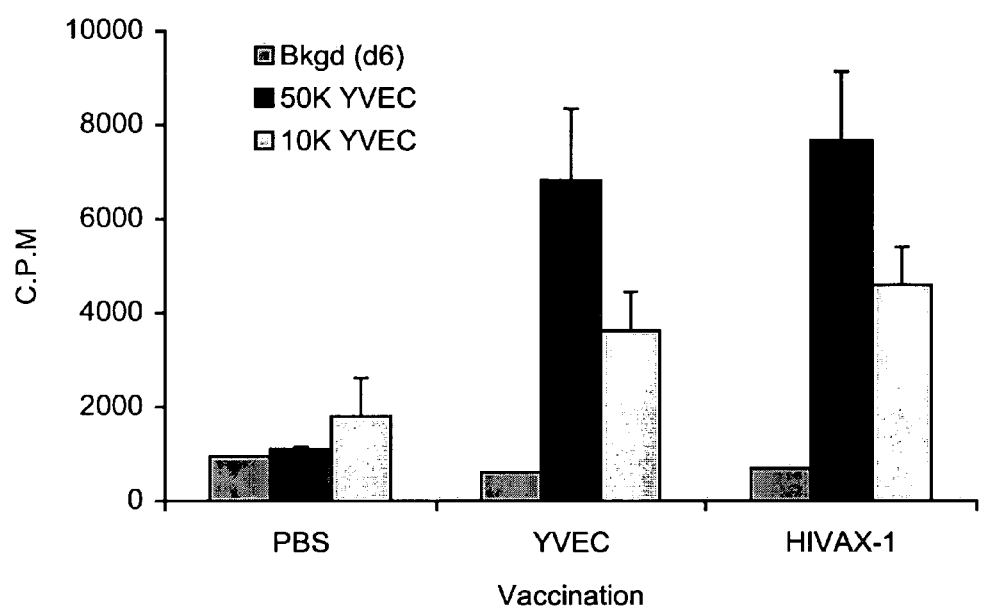
FIG. 6A is a bar graph showing T cell proliferation in cpm after vaccination with YVEC or HIVAX-1.
Figure 6B:
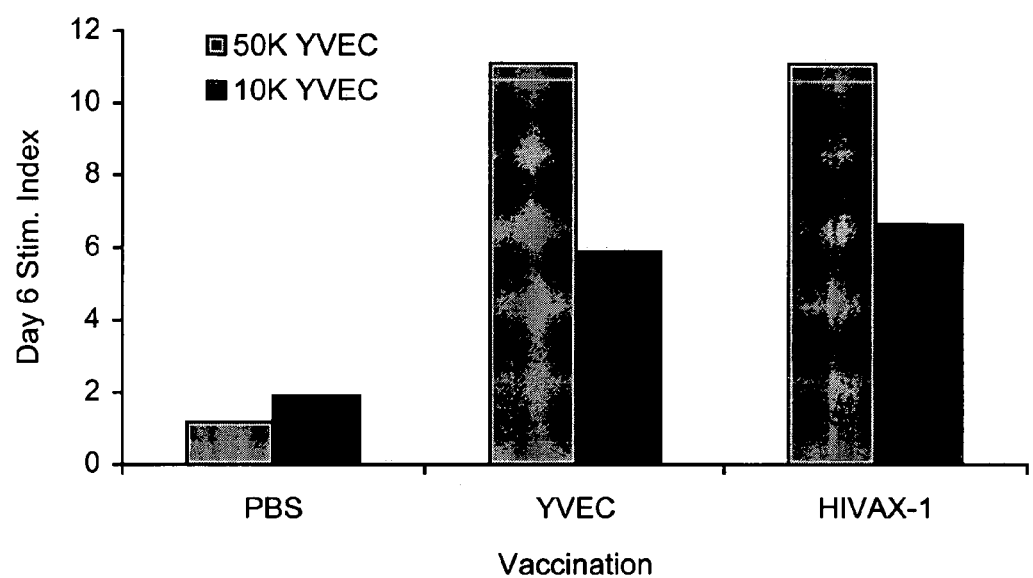
FIG. 6B is a bar graph showing T cell proliferation stimulation indices after vaccination with YVEC or HIVAX-1.

In brief, BALB/c mice were injected with 2×10$^7$ HIVAX-1 yeast, 2×10$^7$ YVEC yeast or PBS on days 0, 7 and 14. Mice were sacrificed on day 35 and spleen and lymph node T cells were restimulated in vitro in the presence of the indicated number of heat-inactivated yeast. Proliferation was determined by pulsing the cultures with 3HTdR on day 6 and harvesting on day 7. Results are presented as C.P.M. +/−S.D. for triplicate determinations. FIGS. 6A and 6B show that vaccination with YVEC or HIVAX induces T cell proliferation in response to yeast antigens.

Example 10

The following example shows that two prior vaccinations with non-recombinant yeast does not prevent the induction or protective immunity by subsequent vaccination with recombinant yeast.

Figure 7:
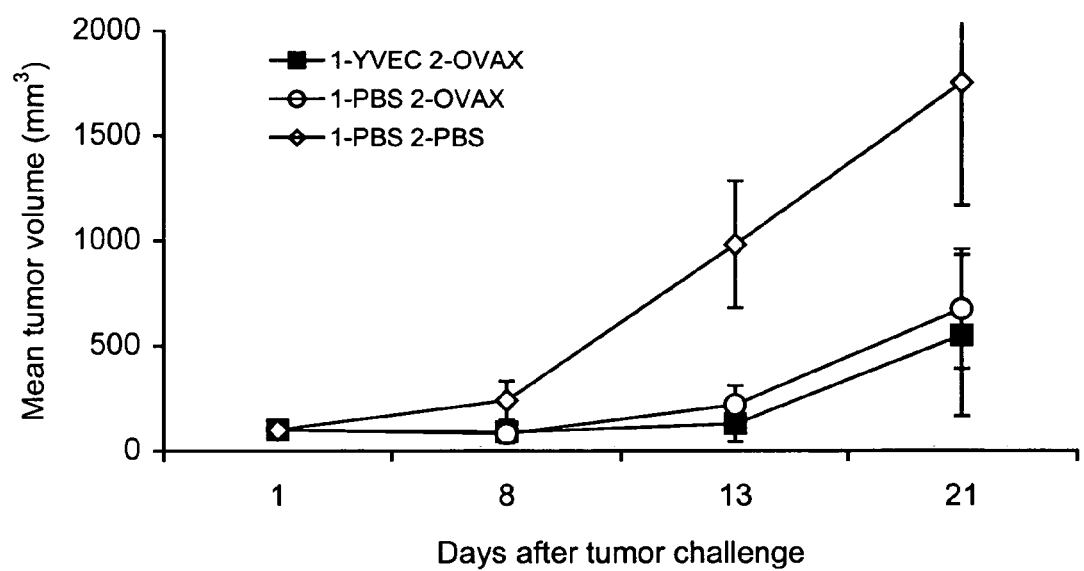
FIG. 7 is a line graph showing EG.7-OVA tumor growth after vaccination with OVAX after previous vaccination with non-recombinant yeast.

In brief, mice were injected (d-14 & d-7) with 2×10$^7$ live YVEC yeast or with PBS. On day 0 and day 7 they were injected with 2×10$^7$ live OVAX yeast or with PBS. On day 14, mice were challenged with E.G7-OVA lymphoma cells. Tumor growth was measured on the indicated day. FIG. 7 shows that mice vaccinated with OVAX show reduced tumor growth even when previously vaccinated with non-recombinant yeast.

Example 11

The following example demonstrates that live recombinant yeast were not pathogenic in immunodeficient scid mice.

In one embodiment, the vaccine protocol for the present invention involves injection of live yeast. In vitro, the yeast do not grow well at neutral pH (7.0–7.4). However, the inventors were concerned that the yeast may grow or survive in vivo. To address this concern, 2×10$^7$ live intact HIVAX-1 yeast or spheroplasts were injected into the peritoneal cavities of immunodeficient CB.17$^{scid}$ mice. The mice were observed for 10 days and showed no evidence of infection (data not shown). In addition, upon sacrifice on day 10, no yeast could be cultured from the peritoneal cavities of the mice (data not shown).

This result shows that the vaccine preparation does not contain infectious material and should be safe to administer to immunocompromised individuals.

Example 12

The following example shows that recombinant yeast are immunogenic in non-human primates.

The inventors were given permission to immunize 9 monkeys by collaborator Dr. Mark Laudenslager with the stipulation that the animals would be sacrificed 30 days later. IACUC approval for vaccination was obtained and immunization was begun with HIVAX-1 and Y-vector (YVEC).

TABLE 1

Vaccination schedule and route for preliminary study in pig-tailed macaques.

| Monkey # | Sex | Vaccine | 12/1 | 12/8 (right arm) and 12/15 (left arm) |
|---|---|---|---|---|
| 1 and 2 | F, M | 1 × 10$^7$ live, intact Y-vector | IP | ½ IM + ½ SC |
| 3 and 4 | M, F | 5 × 10$^7$ live, intact Y-vector | IP | ½ IM + ½ SC |
| 5 and 8 | F, M | 1 × 10$^7$ live, intact HIVAX-1 | IP | ½ IM + ½ SC |
| 6 and 7 | F, M | 5 × 10$^7$ live, intact HIVAX-1 | IP | ½ IM + ½ SC |
| 9 | F | Nothing | IP | Nothing |

Methods. A tissue culture medium (TCM) consisting of RPMI 1640 supplemented with 7.5% heat-inactivated fetal calf serum, L-glutamine, L-pyruvate, nonessential amino acids, vitamins, gentamycin and 2-mercaptoethanol was used for all cell cultures. Supernatants from human and/or macaque peripheral blood mononuclear cells stimulated for 24 hr in the presence of 5 µg/ml concanavalin A (Con A) were used as a source of T cell growth factors for monkey T cells (human/monkey CAS).

At the time of each vaccination, approximately 7 ml of blood was drawn from each monkey. Two ml was allowed to clot for isolation of serum. The remaining 5 ml was immediately mixed with preservative-free heparin, diluted 1:1 with TCM and carefully layered over 95% Histiopaque 1077:5% RPMI 1640. Mononuclear cells were removed from the interface, washed twice and resuspended in TCM for use in in vitro assays. At the time of sacrifice, approximately 50 ml of blood was obtained from each animal and axillary lymph nodes and spleens were harvested. Cell suspensions were prepared from the spleens and lymph nodes by cutting the organs into small pieces followed by Dounce homogenization. Mononuclear cells were isolated as described above. All cell manipulations were performed in the presence of preservative-free heparin to prevent clotting.

Results. Groups of two Pig-tailed macaques were injected weekly for three weeks with 10 million or 50 million recombinant yeast that did or did not express the HIV gp160-SF2 glycoprotein. A single macaque served as an uninjected control. No adverse reactions were observed at the site of the injections. Two tubes of peripheral blood were collected from the animals at the time of each immunization; one was allowed to clot to obtain serum for use in ELISA and Western Blot analyses for anti-gp160-SF2 antibodies (to be performed), the second was used for isolation of mononuclear cells for T cell proliferation and CTL assays. 3–4× 10$^6$ PBMC per ml of whole blood were routinely obtained from the monkeys. 83 days after the first and 69 days after the last vaccination, the animals were sacrificed at which time peripheral blood, axillary lymph nodes and spleen were collected.

T cell proliferation assay results. Cells obtained from animals prior to the first vaccination responded vigorously to mitogenic stimuli (Stimulation indices >50 in response to ConA and PHA and showed variable, but weak responses to heat-killed YVEC or HIVAX-1. Purified gp120-SF2 was not available until just before the animals were sacrificed. At the time of the second immunization, the T cell proliferation assays were repeated with Con A and heat-killed YVEC and HIVAX-1. The proliferation assays showed a dose-response with increasing proliferation observed with increasing numbers of yeast added. By two weeks after the first vaccination, the vaccine recipients clearly demonstrated an enhanced proliferative response to live or heated yeast as compared to monkey #9 which had not been vaccinated.

TABLE 2

Macaque T cell proliferative responses to yeast antigens

| Day of assay | Non-vaccinated | YVEC | HIVAX-1 |
|---|---|---|---|
| 0 - prior to first vaccination | 3.1 ± 0.6 | 1.8 ± 0.9 | 2.0 ± 0.6 |
| 7 - prior to second vaccination | 2.0 ± 0.5 | 3.5 ± 0.6 | 2.3 ± 1.3 |
| 14 - prior to third vaccination | 1.5 ± 1.0 | 12.5 ± 3.0 | 6.8 ± 1.0 |
| 65 | 2.2 ± 1.0 | 9.5 ± 2.5 | 6.0 ± 1.4 |
| 83 - at time of sacrifice | 1.8 ± 1.1 | 8.3 ± 3.0 | 9.7 ± 1.5 |

Results showed that, sixty-nine days after the final vaccination, monkeys vaccinated with Y-vector (YVEC) or HIVAX-1 retained the ability to respond to yeast antigens. The response was variable depending on the source of lymphocytes used (PBMC, LN, SPL) but in all cases showed a dose-response depending on the amount of yeast which were included in the assay. The response increased from day 2 to day 4 (these days were chosen for assay based on preliminary studies with PBMC). Importantly, lymphocyte populations from monkeys vaccinated with HIVAX-1, but not with Y-vector, also responded to purified gp120-SF2 (yeast and CHO-derived).

CTL generation. At the time of sacrifice, macaque lymphocytes were cultured in the presence of HIVAX-1 yeast as had been done for the mice studies. In brief, ten million macaque PBMC, LN or spleen cells were placed in 10 ml TCM with one million heated HIVAX-1 yeast. On day 5 after initiation of culture, macaque CAS and rhIL-2 were added to a final concentration of 10% and 10 U/ml respectively. The cells were fed weekly by adding 5 ml TCM+ growth factors. Flow cytometric analysis of the PBMC on day 14 after initiation of culture revealed greater than 98% CD2 bearing cells (using anti-human CD2 which cross-reacts with macaque CD2). 50–60% of the cells expressed CD8 with 30–50% expressing CD4. When stimulated with 0.5 µg/ml Ionomycin and 5 ng/ml PMA, the macaque cells were able to kill human CEM cells (data not shown) suggesting that the cultures contained CTL. Unfortunately, the cells could not be tested for killing as the inventors were unable to generate autologous transformed cell lines or keratinocytes for use as targets. The inventors attempted to use the effector cell populations themselves as targets but were unable to infect them with vaccinia virus (no cytopathic effects were observed, suggesting that they were not infected). $^{51}$Cr labeling and spontaneous release values obtained suggested that the cells would not have been suitable as targets even if the problem with infection had not arisen. Thus despite the desire to examine antigen-specific CTL activity in the macaques, this was not achieved.

Nonetheless, these studies in macaques showed that the vaccine was safe to administer and is predicted to induce antigen-specific T cell responses in a second species of animal.

Example 13

The following example demonstrates the development of an HIV vaccine for human clinical trial.

Figure 8:
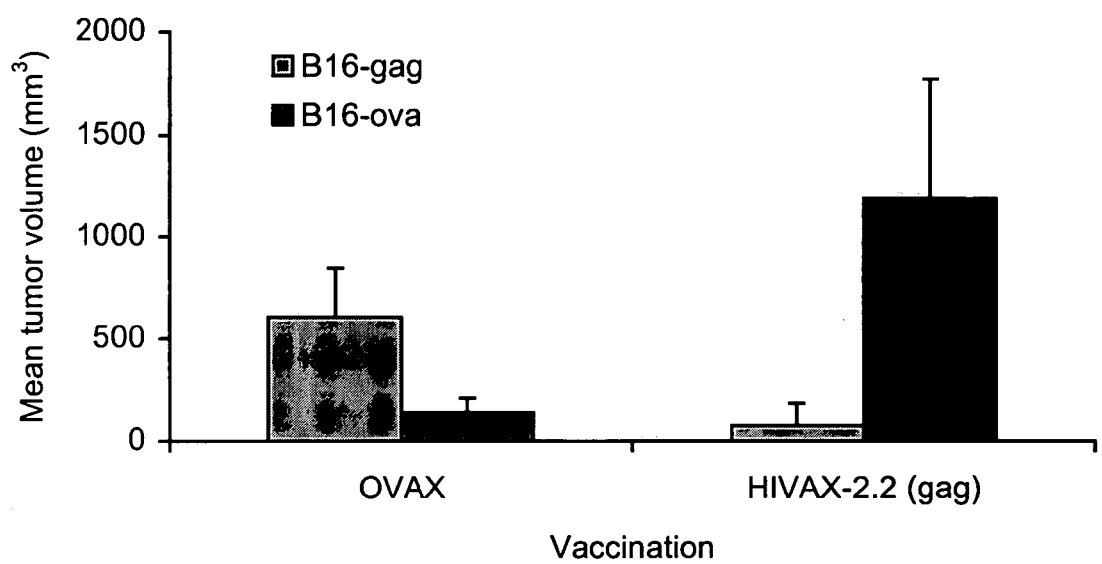
FIG. 8 is a bar graph showing tumor growth after vaccination with OVAX or HIVAX.

The following experiment demonstrates that a candidate recombinant yeast-based HIV vaccine encoding gag protein provides antigen-specific immunity against melanoma cells expressing gag but not ova. In brief, 6 week old female C57B1/6 mice were vaccinated sub-cutaneously on days 0 and 7 with $2 \times 10^7$ live HIVAX-2.2 (gag) yeast or $2 \times 10^7$ live OVAX yeast. Mice were challenged with $2.5 \times 10^4$ B16-gag or $1 \times 10^5$ B16-ova cells on day 14. Tumor growth was measured on day 20. FIG. 8 shows that mice vaccinated with OVAX had reduced growth of tumors expressing ovalbumin as compared to gag, and that mice vaccinated with HIVAX had reduced growth of tumors expressing gag as compared to ova, demonstrating that the vaccination was antigen-specific.

Figure 11A:
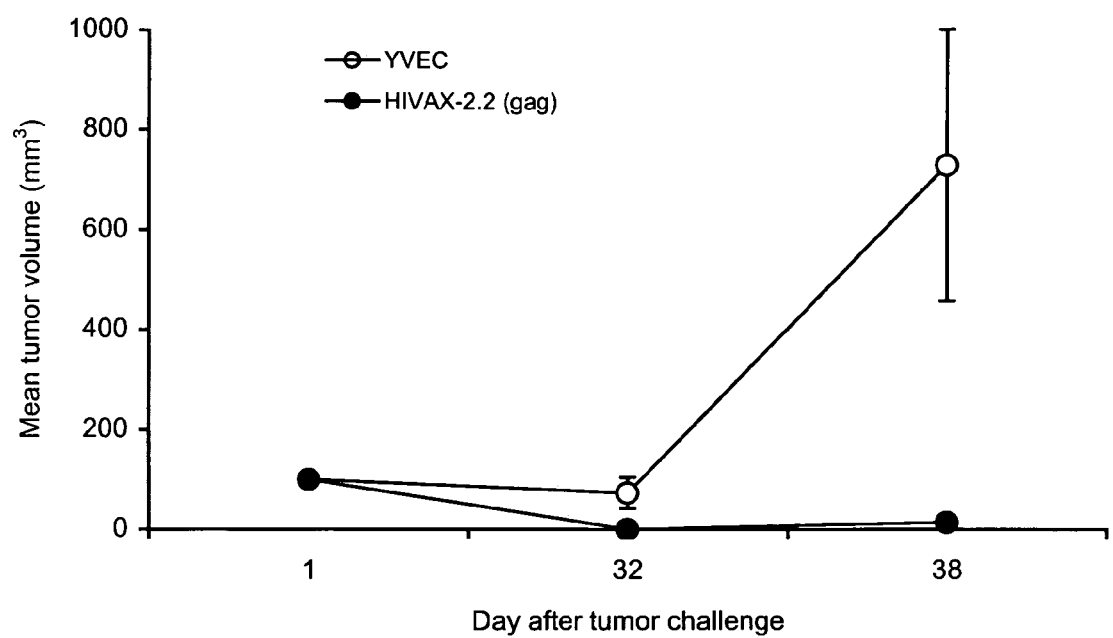
FIG. 11A is a line graph showing tumor growth after nasal vaccination with HIVAX.

The following experiment shows that the recombinant yeast-based HIV vaccine induces antigen-specific immunity upon nasal inhalation administration in mice. In brief, 6 week old female C57B1/6 mice were vaccinated via intra-nasal inhalation on days 0 and 30 with $2 \times 10^7$ live YVEC yeast or $2 \times 10^7$ live HIVAX-2.2 (gag) yeast. Mice were challenged with $2.5 \times 10^4$ B16-gag cells on day 14. Tumor growth was measured on day 32 and 38. FIG. 11A shows that mice receiving HIVAX by nasal administration showed prolonged reduction in tumor growth as compared to the control, YVEC.

Figure 11B:
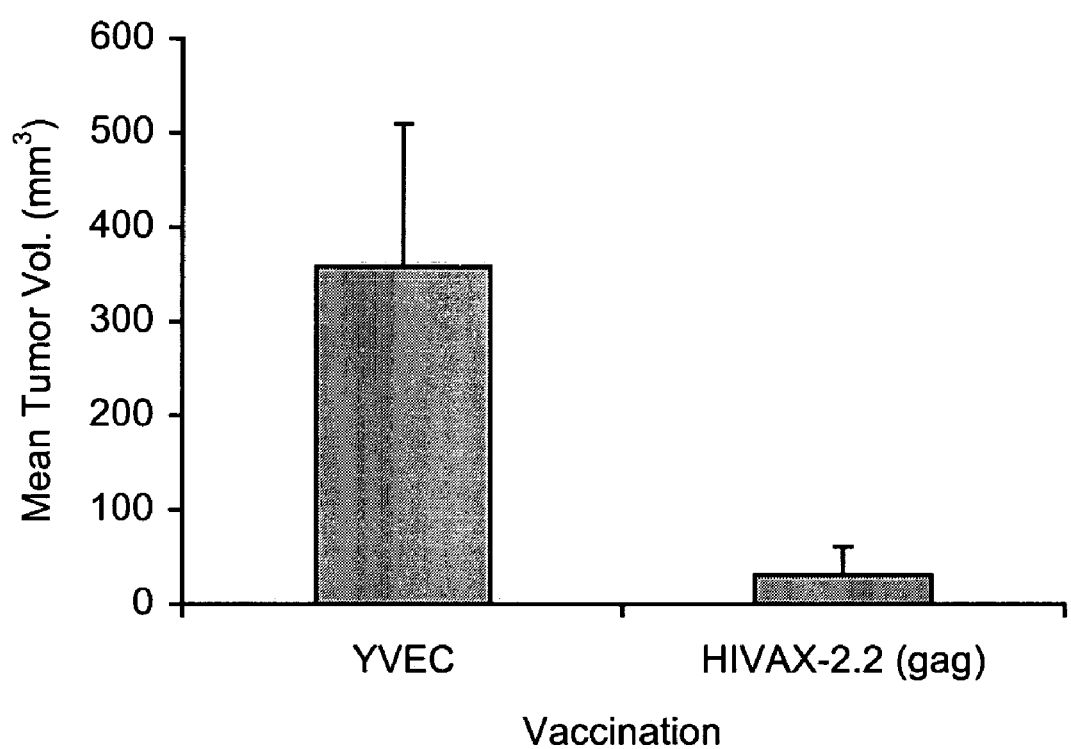
FIG. 11B is a bar graph showing tumor growth after nasal vaccination with HIVAX and YVEC.

In a second experiment using nasal administration, 6 week old female C57B1/6 mice were vaccinated via intra-nasal inhalation on days 0 and 7 with $2 \times 10^7$ live YVEC yeast or $2 \times 10^7$ live HIVAX-2.2 (gag) yeast. Mice were challenged with $2.5 \times 10^4$ B16-gag cells on day 14. Tumor growth was measured on day 21. FIG. 11B shows that mice vaccinated by nasal administration with HIVAX showed reduction in tumor growth as compared to mice vaccinated with YVEC.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

SEQUENCE LISTING

```
<160> NUMBER OF SEQ ID NOS: 1

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
1               5
```

Figure 9:
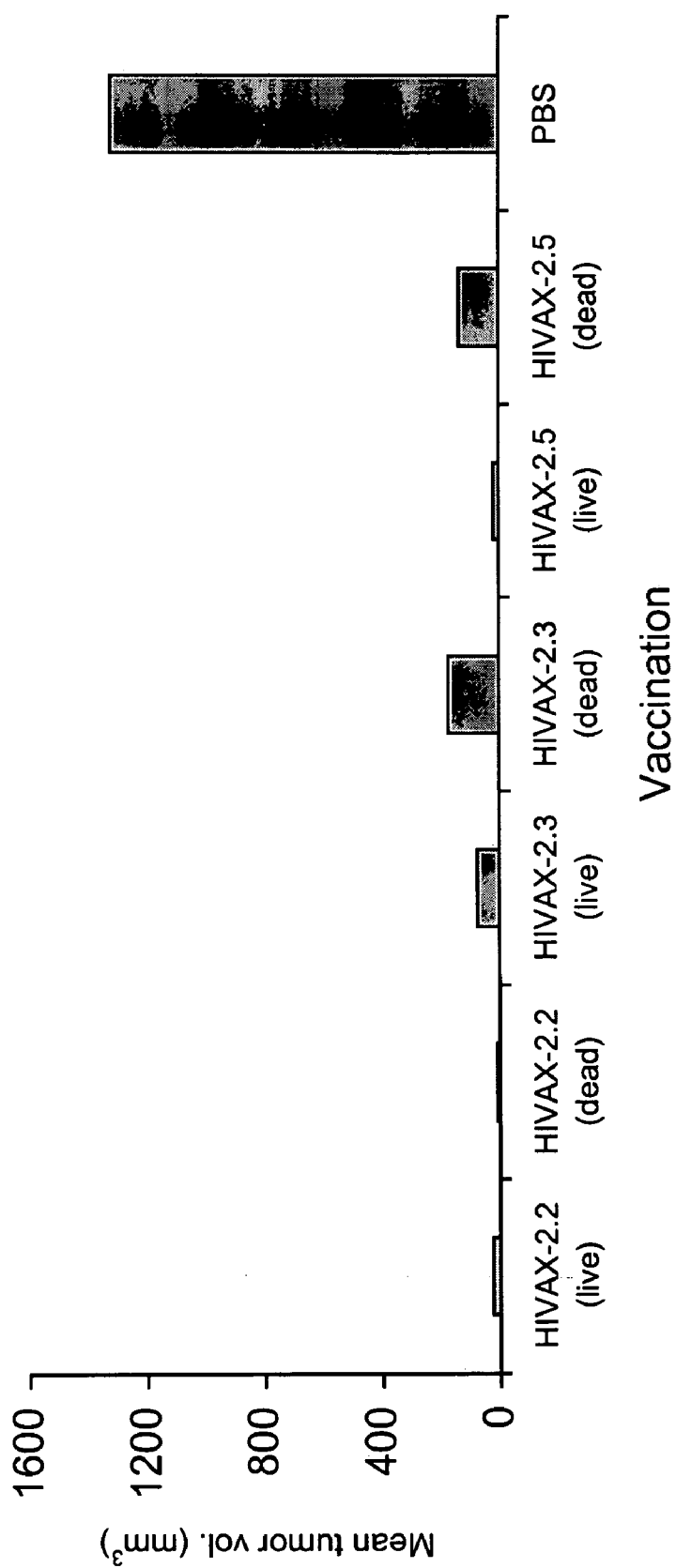
FIG. 9 is a bar graph showing tumor growth after vaccination with heat-killed or live HIVAX.

The following experiment compares three versions of a candidate recombinant yeast-based HIV vaccine encoding gag protein but utilizing different types of yeast promoters, and shows that heat-killed (56° C.×10 min) yeast are as effective as live yeast at inducing protective immunity. In brief, 6 week old female C57B1/6 mice were vaccinated sub-cutaneously on days 0 and 7 with PBS, $2 \times 10^7$ live HIVAX-2 (gag) yeast, or $2 \times 10^7$ heat-killed HIVAX-2 (gag) yeast. The various HIVAX-2 (gag) vaccines differ in terms of the type of promoter used (inducible vs. constitutive) and whether the plasmid is integrated or episomal. Mice were challenged with $2.5 \times 10^4$ B16-gag cells on day 14. Tumor growth was measured on day 28. FIG. 9 shows that both heat-killed and live yeast vaccines reduce tumor growth in the mice.

Figure 10:
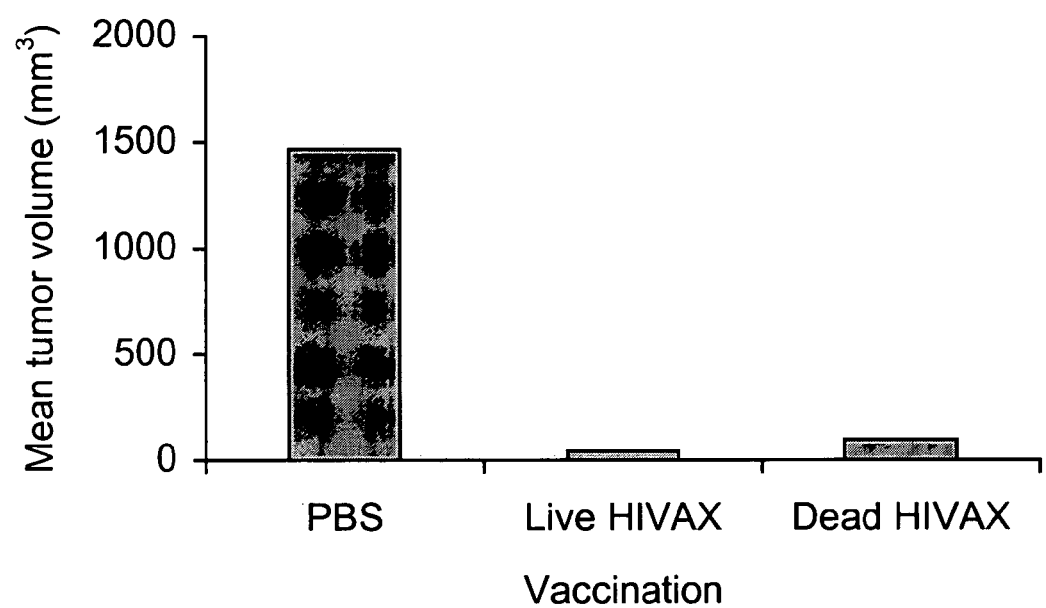
FIG. 10 is a bar graph showing tumor growth after vaccination with heat-killed or live HIVAX.

The following experiment demonstrates that heat-killed (56° C.×10 min) yeast are as effective as live yeast at inducing protective immunity. In brief, 6 week old female C57B1/6 mice were vaccinated sub-cutaneously on days 0 and 7 with PBS, $2 \times 10^7$ live HIVAX-2.3 (gag) yeast, or $2 \times 10^7$ heat-killed HIVAX-2.3 (gag) yeast. Mice were challenged with $2.5 \times 10^4$ B16-gag cells on day 14. Tumor growth was measured on day 28. FIG. 10 shows that heat-killed yeast reduce tumor growth in mice at a level similar to live yeast vaccine.

What is claimed is:

1. An immunogenic composition, comprising:
   a) an isolated dendritic cell;
   b) a yeast vehicle selected from the group consisting of: a whole yeast, a yeast spheroplast, a yeast cytoplast, a yeast ghost, and a subcellular yeast particle; and,
   c) at least one immunogen that is heterologous to the yeast vehicle and that is not expressed by or loaded into the yeast vehicle;
   wherein said dendritic cell has been loaded intracellularly with said yeast vehicle and said at least one immunogen.

2. The immunogenic composition of claim 1, wherein said immunogen is selected from the group consisting of viral antigens, mammalian cell surface molecules, bacterial antigens, fungal antigens, protozoan antigens, helminth antigens, ectoparasite antigens, and cancer antigens.

3. The immunogenic composition of claim 1, wherein said immunogen is selected from the group consisting of: HIV-1 gag, HIV-1 env, HIV-1 pol, HIV-1 tat, HIV-1 nef, HbsAG, HbcAg, hepatitis c core antigen, HPV E6 and E7, HSV glycoprotein D, and *Bacillus anthracis* protective antigen.

4. The immunogenic composition of claim 1, wherein said composition comprises multiple immunogens.

5. The immunogenic composition of claim 1, wherein said composition further comprises at least one biological response modifier.

6. The immunogenic composition of claim 1, wherein said yeast vehicle is selected from the group consisting of: a whole yeast, a yeast spheroplast, a yeast cytoplast, and a yeast ghost.

7. The immunogenic composition of claim 1, wherein said yeast vehicle is selected from the group consisting of: a whole yeast and a yeast spheroplast.

8. The immunogenic composition of claim 1, wherein said yeast vehicle is a whole yeast.

9. The immunogenic composition of claim 1, wherein said yeast is a nonpathogenic yeast.

10. The immunogenic composition of claim 1, wherein said yeast is of a genus selected from the group consisting of *Saccharomyces, Candida, Cryptococcus, Hansenula, Kluyveromyces, Pichia, Rhodotorula, Schizosaccharomyces* and *Yarrowia*.

11. A method to produce an immunogenic composition, comprising loading a dendritic cell intracellularly with:
   a) a yeast vehicle selected from the group consisting of: a whole yeast, a yeast spheroplast, a yeast cytoplast, a yeast ghost, and a subcellular yeast particle; and,
   b) at least one immunogen that is heterologous to said yeast vehicle and that is not expressed by or loaded into the yeast vehicle.

12. The method of claim 11, wherein said step of loading a dendritic cell is accomplished by a method selected from the group consisting of: diffusion, active transport, liposome fusion, electroporation, phagocytosis, and bath sonication.

13. An immunogenic composition produced by the method of claim 11.

14. A method to elicit an antigen-specific humoral immune response and an antigen-specific cell-mediated immune response in a mammal, said method comprising administering to said mammal the immunogenic composition of claim 1.

15. The method of claim 14, wherein said immunogenic composition is administered by a route selected from the group consisting of: intravenous, intraperitoneal, subcutaneous, intradermal, intranodal, intramuscular, transdermal, inhaled, intranasal, oral, intraocular, intraarticular, intracranial, and intraspinal.

16. The method of claim 14, wherein said immunogenic composition is administered with a pharmaceutically acceptable excipient.

17. A method to elicit an antigen-specific humoral immune response and an antigen-specific cell-mediated immune response in a mammal, said method comprising administering to said mammal the immunogenic composition of claim 13.

* * * * *